(12) United States Patent
Imai

(10) Patent No.: US 10,542,867 B2
(45) Date of Patent: Jan. 28, 2020

(54) ENDOSCOPE

(71) Applicant: OLYMPUS CORPORATION, Tokyo (JP)

(72) Inventor: Shunichi Imai, Okaya (JP)

(73) Assignee: OLYMPUS CORPORATION, Tokyo (JP)

( * ) Notice: Subject to any disclaimer, the term of this patent is extended or adjusted under 35 U.S.C. 154(b) by 120 days.

(21) Appl. No.: 15/294,864

(22) Filed: Oct. 17, 2016

(65) Prior Publication Data

US 2017/0027421 A1    Feb. 2, 2017

Related U.S. Application Data

(63) Continuation of application No. PCT/JP2016/050934, filed on Jan. 14, 2016.

(30) Foreign Application Priority Data

Jan. 27, 2015  (JP) .................................. 2015-013599

(51) Int. Cl.
    *A61B 1/00* (2006.01)
    *A61B 1/05* (2006.01)

(52) U.S. Cl.
    CPC ........ *A61B 1/00101* (2013.01); *A61B 1/0011* (2013.01); *A61B 1/00073* (2013.01);
    (Continued)

(58) Field of Classification Search
    CPC ............ A61B 1/00064; A61B 1/00071; A61B 1/0008; A61B 1/00089; A61B 1/00091;
    (Continued)

(56) References Cited

U.S. PATENT DOCUMENTS

2012/0316395 A1\* 12/2012 Koga ................. A61B 1/00091
600/157

FOREIGN PATENT DOCUMENTS

JP    H05-184522 A    7/1993
JP    H11-197095 A    7/1999
(Continued)

OTHER PUBLICATIONS

International Search Report dated Apr. 12, 2016 issued in PCT/JP2016/050934.

*Primary Examiner* — Ryan N Henderson
(74) *Attorney, Agent, or Firm* — Scully, Scott, Murphy & Presser, P.C.

(57) ABSTRACT

An endoscope includes: a distal end cover provided on a distal end of an insertion portion; a holding member fitted with the distal end cover and holding built-in components; a cylindrical member inserted into the distal end cover and the holding member, the cylindrical member having a groove portion formed on an outer circumference; an elastically deformable elastic member engageably inserted into the groove portion and fixing the cylindrical member to the distal end cover and the holding member; first accommodating portions formed at least on a surface of the holding member and accommodating the elastic member; and second accommodating portions communicating to the first accommodating portions and accommodating the elastic member which, at time of inserting and detaching the cylindrical member, comes out from the groove of the cylindrical member, comes into contact with the outer circumferential portion of the cylindrical member and bends by elastic deformation.

5 Claims, 22 Drawing Sheets

(52) U.S. Cl.
CPC ...... *A61B 1/00091* (2013.01); *A61B 1/00096* (2013.01); *A61B 1/00137* (2013.01); *A61B 1/05* (2013.01)

(58) Field of Classification Search
CPC ............ A61B 1/00094; A61B 1/00096; A61B 1/00101; A61B 1/0011; A61B 1/00112; A61B 1/00119; A61B 1/00137; A61B 1/012; A61B 1/015; A61B 1/05; A61B 1/051; A61B 1/053; A61B 1/0661; A61B 1/0676; A61B 1/126; A61B 1/127; A61B 1/128
See application file for complete search history.

(56) References Cited

FOREIGN PATENT DOCUMENTS

| | | | |
|---|---|---|---|
| JP | H11-244222 A | | 9/1999 |
| JP | 2005-253511 A | | 9/2005 |
| JP | 2013128710 A | * | 7/2013 |

* cited by examiner

ENDOSCOPE

CROSS REFERENCE TO RELATED APPLICATION

This application is a continuation application of PCT/JP2016/050934 filed on Jan. 14, 2016 and claims benefit of Japanese Application No. 2015-013599 filed in Japan on Jan. 27, 2015, the entire contents of which are incorporated herein by this reference.

BACKGROUND OF THE INVENTION

1. Field of the Invention

The present invention relates to an endoscope with various kinds of units fixed to a distal end portion of an insertion portion.

2. Description of the Related Art

As is well known, endoscopes are widely used for observation, treatment and the like inside a body (inside a body cavity) of a living body or for inspection, repair and the like in industrial plant equipment.

On such an endoscope, an image pickup unit in which an objective optical system is arranged, an illumination unit in which an illumination optical system is arranged, a channel unit for a treatment instrument channel, a nozzle unit such as for air/water feeding, and the like are fixed to a distal end portion by screw members.

The various kinds of units are fitted by screwing screws into tapped screw holes made in a distal end portion body provided on the distal end portion of the endoscope, and further bonded and fixed so that the screws do not loosen.

For example, Japanese Patent Application Laid-Open Publication No. H11-244222 discloses a structure for attaching a fluid jet nozzle of an endoscope in which the fluid jet nozzle to be detachably fitted to a distal end rigid portion can be easily attached and detached, and when being fitted, the fluid jet nozzle is fixed firmly in a stable state.

SUMMARY OF THE INVENTION

An endoscope of an aspect of the present invention is provided with: an insertion portion configured to be inserted into a subject; a distal end cover provided on a distal end of the insertion portion; a holding member fitted with the distal end cover and configured to hold built-in components of the insertion portion; a cylindrical member configured to be inserted into the distal end cover and the holding member, the cylindrical member having a groove portion formed on an outer circumference; an elastically deformable elastic member configured to be engageably inserted into the groove portion of the cylindrical member and fix the cylindrical member to the distal end cover and the holding member; a first accommodating portion formed at least on a surface of the holding member on which the distal end cover is fitted and configured to accommodate the elastic member; and a second accommodating portion communicating to the first accommodating portion and configured to, when the cylindrical member is inserted into or detached from the distal end cover and the holding member, accommodate the elastic member bent by elastic deformation by coming into contact with the outer circumferential portion of the cylindrical member.

DETAILED DESCRIPTION OF THE PREFERRED EMBODIMENT(S)

An endoscope which is the present invention will be described below. Note that it should be noticed that drawings based on each embodiment are schematic in the description below, and a relationship between thickness and width of each portion, a thickness ratio among respective portions and the like are different from actual ones. Among the drawings, portions having different dimension relationship or ratios may be included.

Note that, though the endoscope in description of components below will be described, with a so-called flexible endoscope whose insertion portion is flexible so as to be inserted into an upper or lower digestive organ of a living body given as an example, the endoscope is, however, not limited to the flexible endoscope but is a technique applicable to a so-called rigid endoscope whose insertion portion is rigid to be used for surgery.

(First Embodiment)

Figure 1:
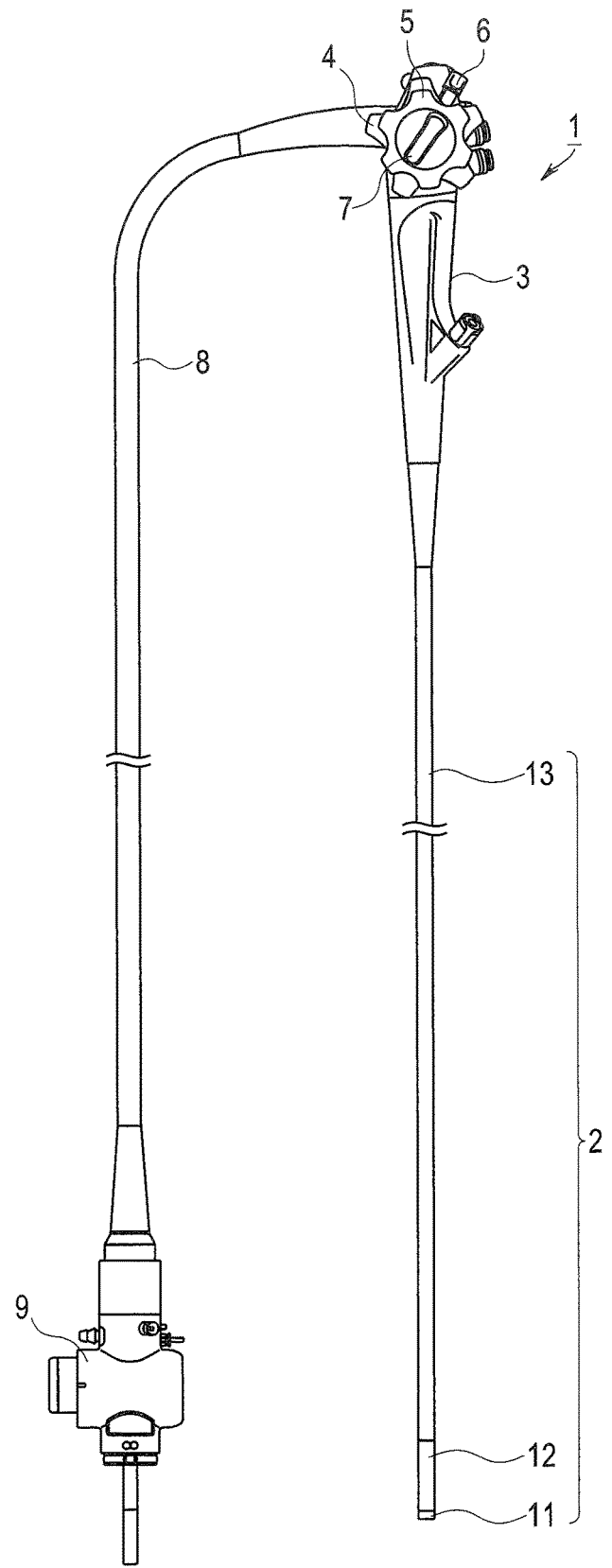
FIG. 1 is a plan view showing an entire configuration of an endoscope according to an aspect of the present invention.
Figure 2:
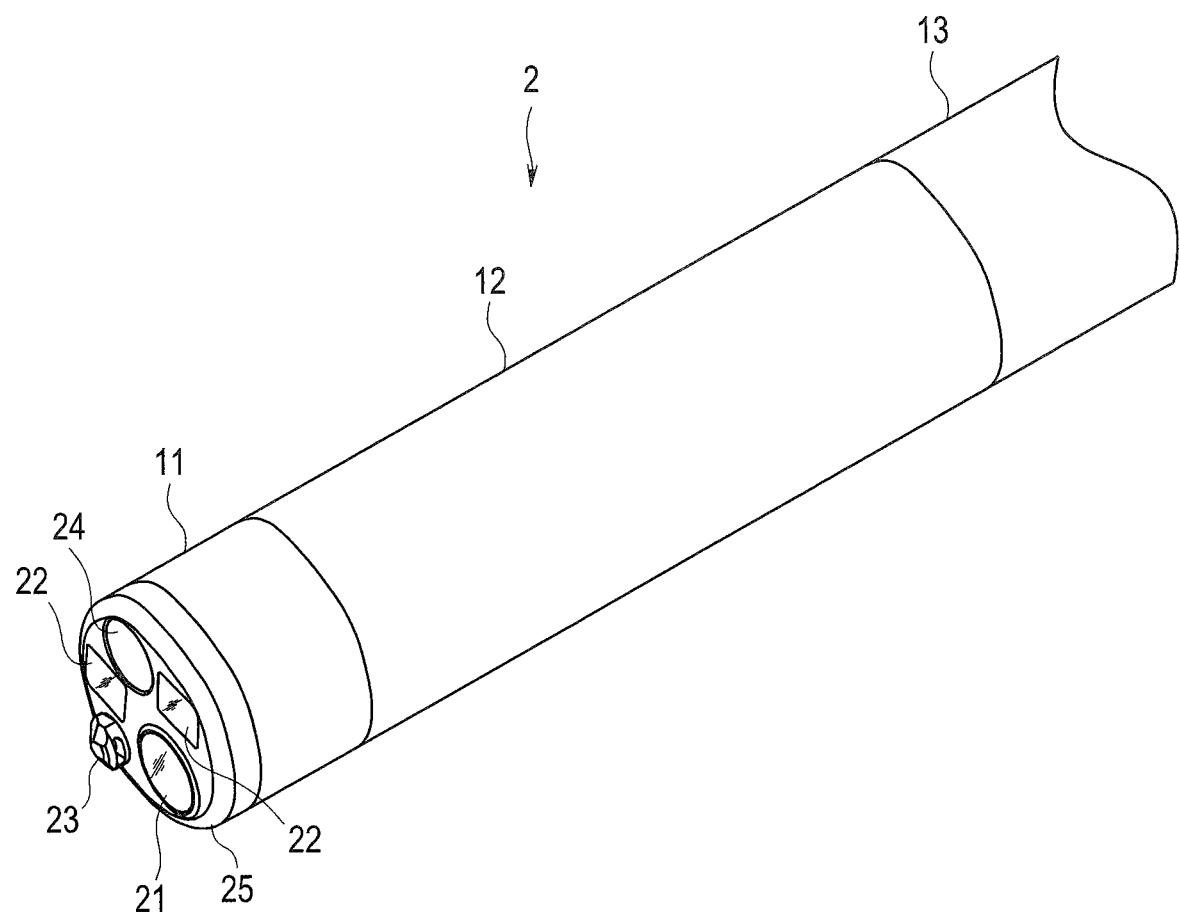
FIG. 2 is a perspective view showing a configuration of an insertion portion according to the aspect of the present invention.
Figure 3:
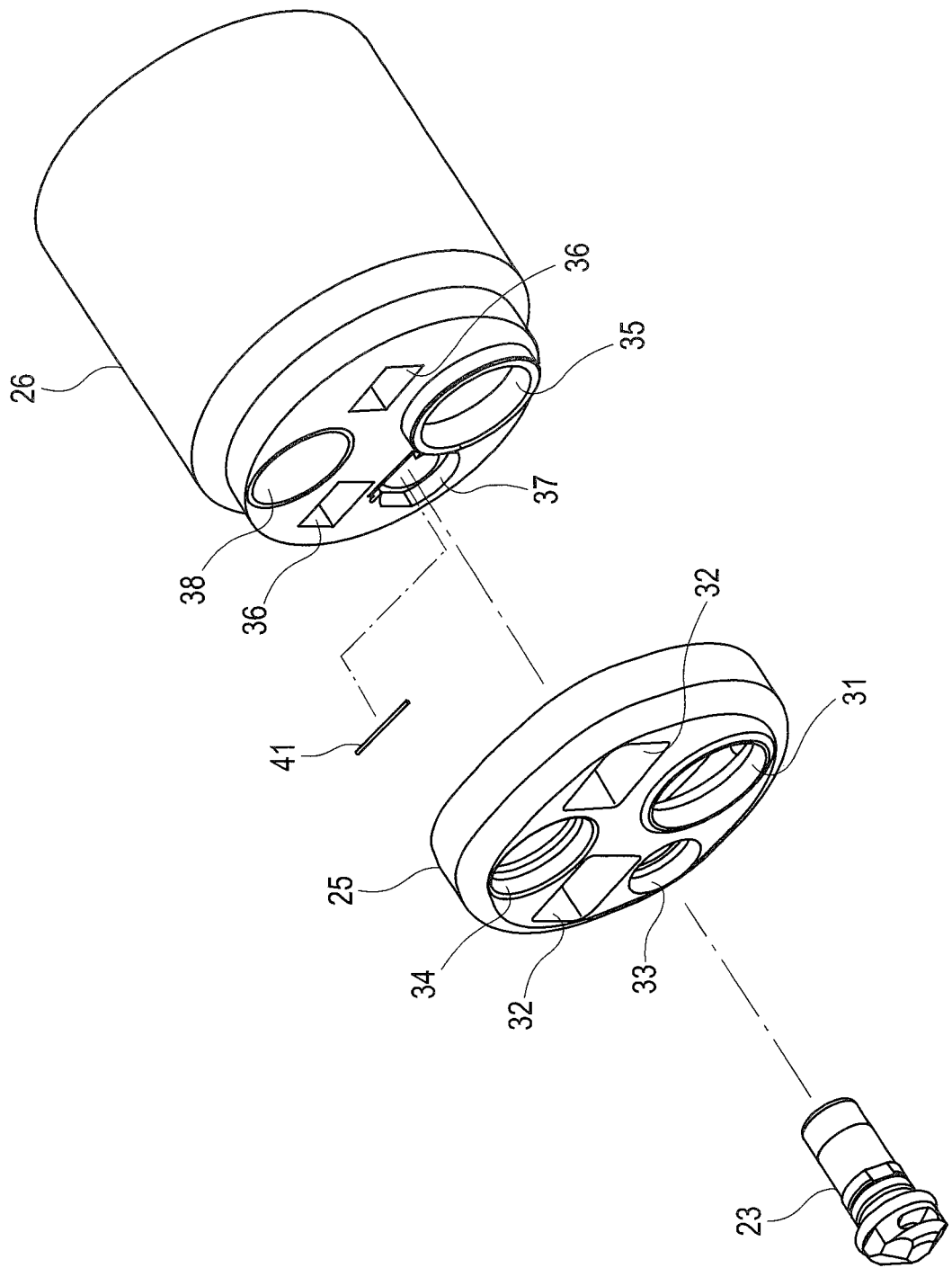
FIG. 3 is an exploded perspective view showing a configuration of a distal end portion according to the aspect of the present invention.
Figure 4:
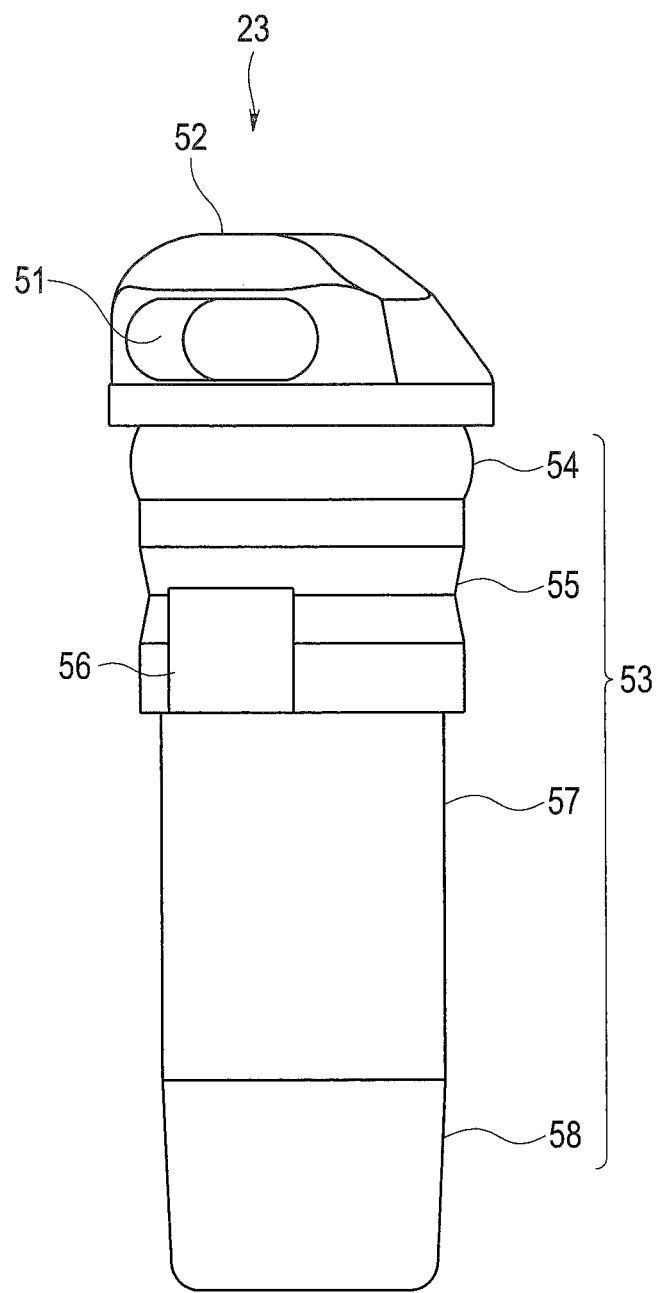
FIG. 4 is a perspective view showing a configuration of an air/water feeding nozzle according to the aspect of the present invention.
Figure 5:
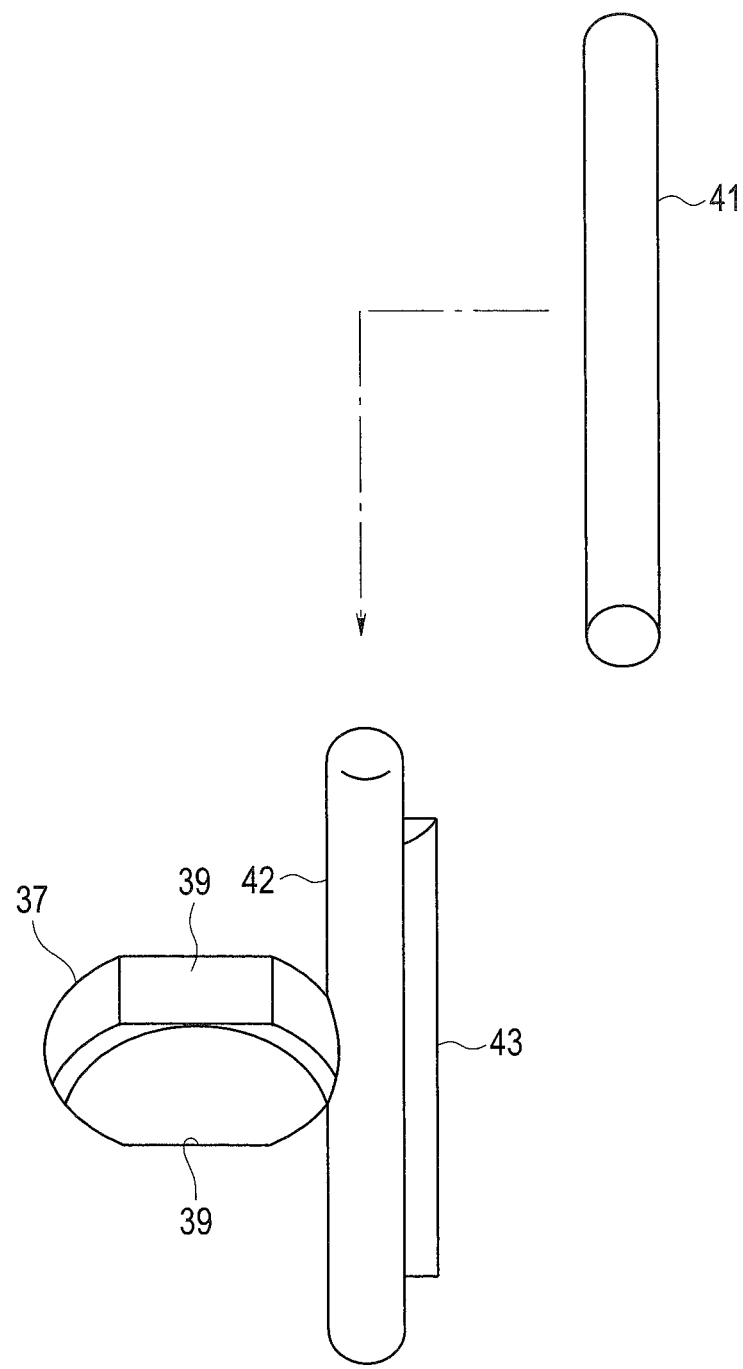
FIG. 5 is a perspective view showing a configuration of a nozzle holding hole formed in a distal end rigid portion, a pin setting groove in which a pin is to be set, and a pin relief groove, according to the aspect of the present invention.
Figure 6:
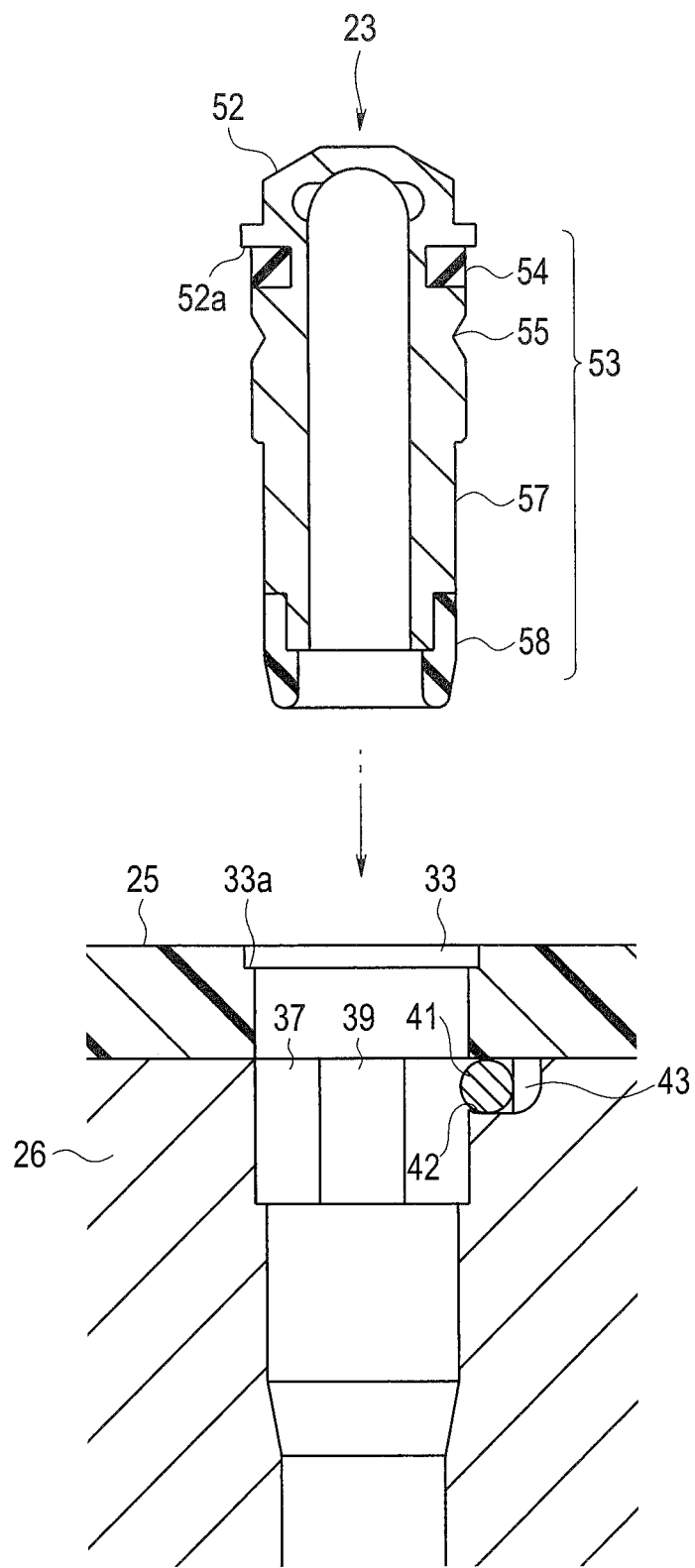
FIG. 6 is a cross-sectional view showing a state before the air/water feeding nozzle is fitted to the distal end portion, according to the aspect of the present invention.
Figure 7:
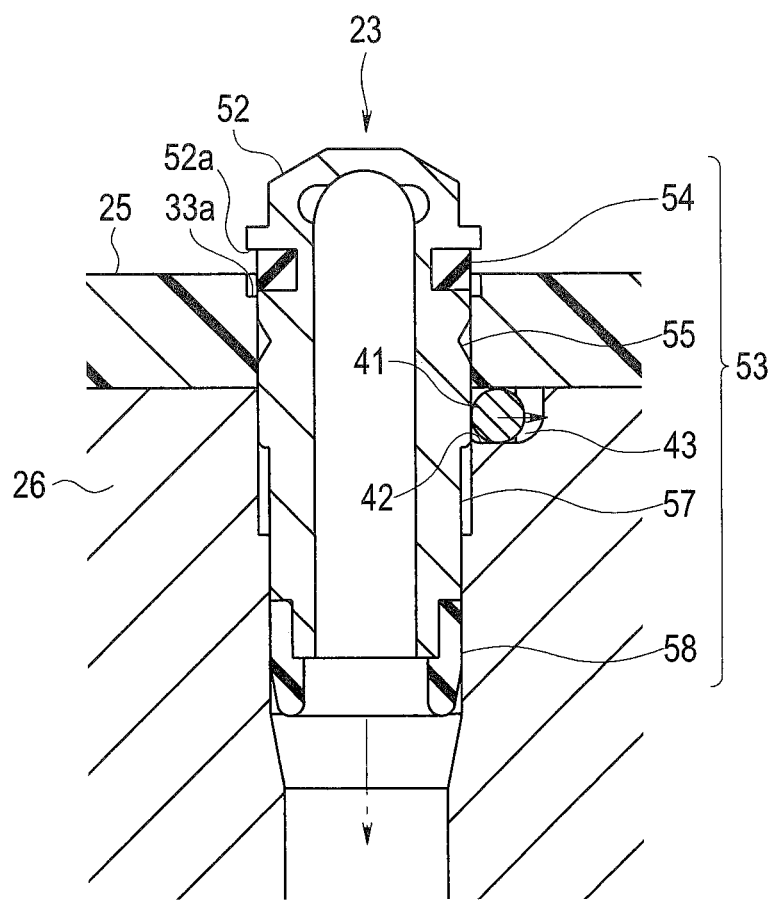
FIG. 7 is a cross-sectional view showing a state while the air/water feeding nozzle is being fitted to the distal end portion, according to the aspect of the present invention.
Figure 8:
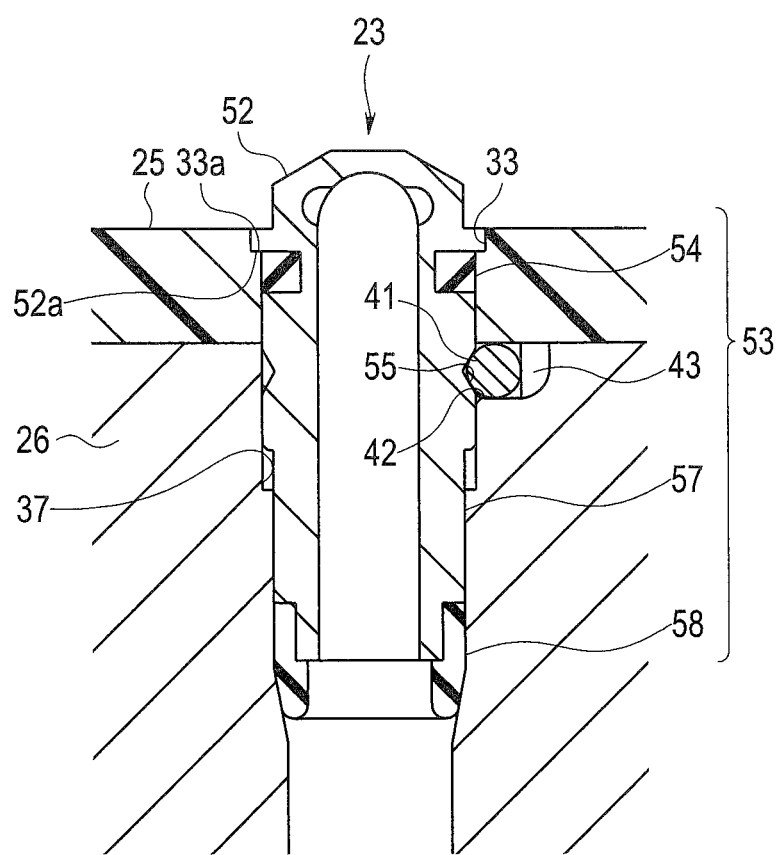
FIG. 8 is a cross-sectional view showing a state that the air/water feeding nozzle has been fitted to the distal end portion, according to the aspect of the present invention.
Figure 9:
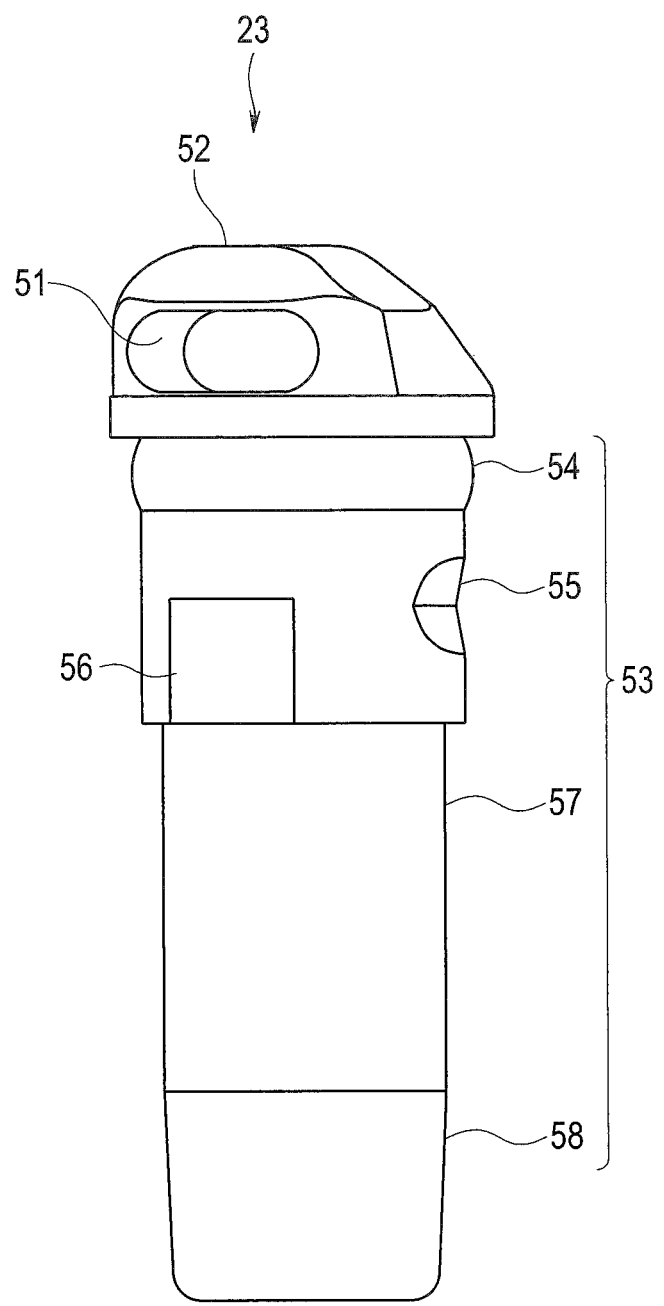
FIG. 9 is a perspective view showing a configuration of the air/water feeding nozzle according to a first modification of the aspect of the present invention.
Figure 10:
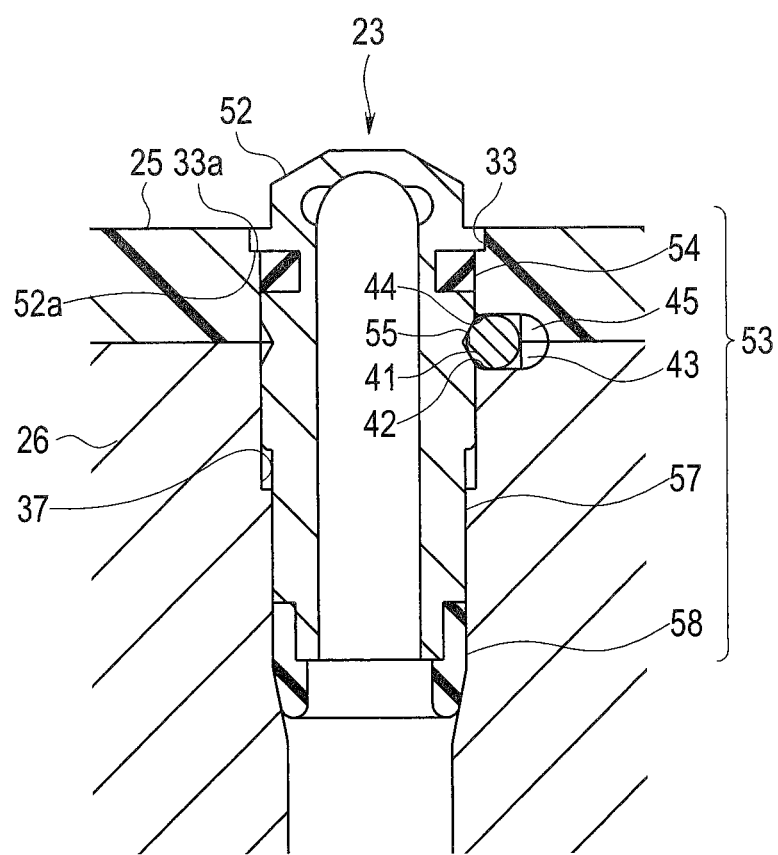
FIG. 10 is a cross-sectional view showing a state that the air/water feeding nozzle has been fitted to the distal end portion, according to a second modification of the aspect of the present invention.
Figure 11:
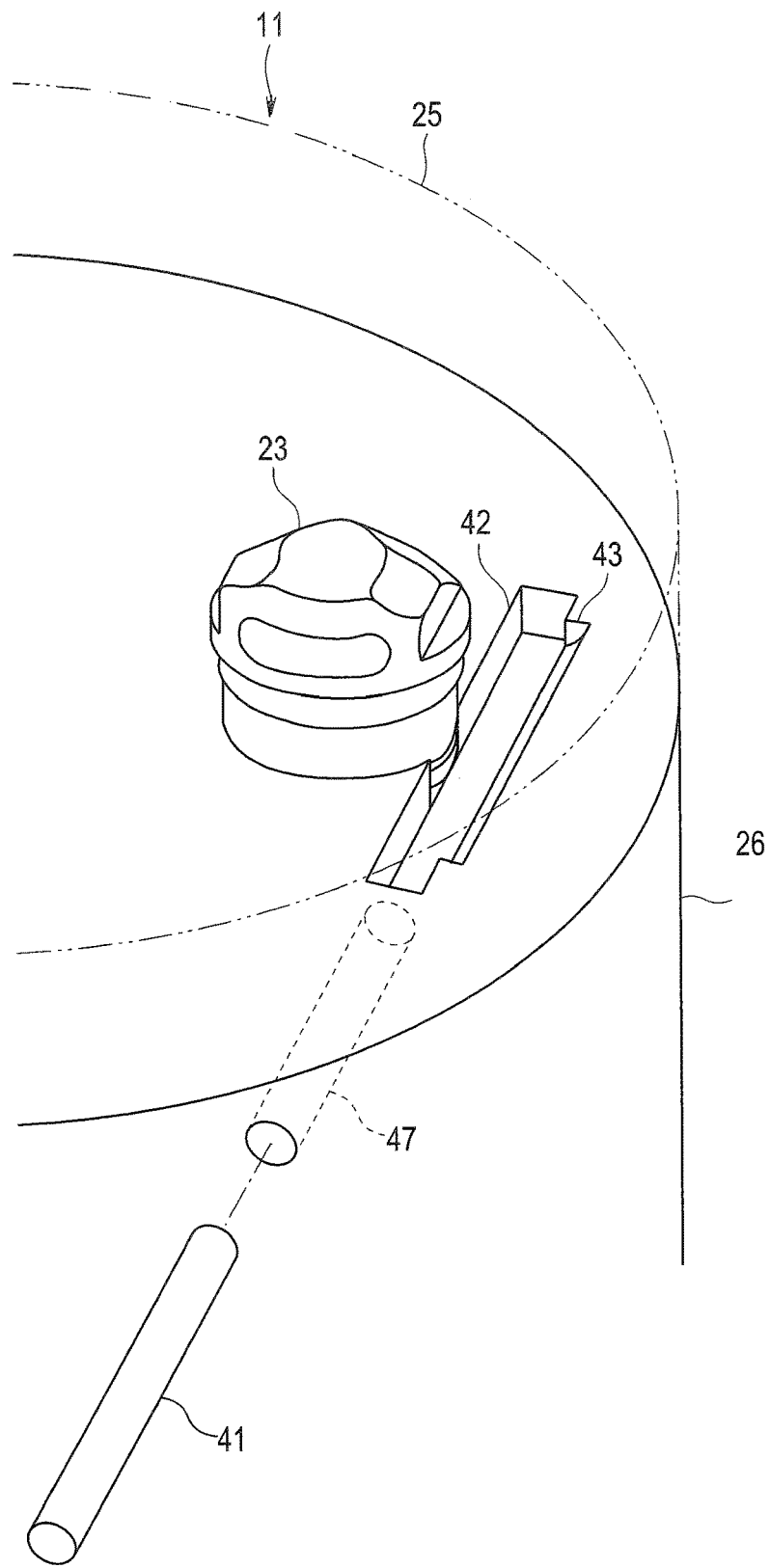
FIG. 11 is a perspective view partially showing the distal end portion to which the air/water feeding nozzle has been fitted, according to a third modification of the aspect of the present invention.

First, a part fixation structure of an endoscope of an aspect of the present invention will be described based on drawings. FIG. 1 is a plan view showing an entire configuration of an endoscope according to an aspect of the present invention; FIG. 2 is a perspective view showing a configuration of an insertion portion; FIG. 3 is an exploded perspective view showing a configuration of a distal end portion; FIG. 4 is a perspective view showing a configuration of an air/water feeding nozzle; FIG. 5 is a perspective view showing a configuration of a nozzle holding hole formed in a distal end rigid portion, a pin setting groove in which a pin is to be set, and a pin relief groove; FIG. 6 is a cross-sectional view showing a state before the air/water feeding nozzle is fitted to the distal end portion; FIG. 7 is a cross-sectional view showing a state while the air/water feeding nozzle is being fitted to the distal end portion; FIG. 8 is a cross-sectional view showing a state that the air/water feeding nozzle has been fitted to the distal end portion; FIG. 9 is a perspective view showing a configuration of the air/water feeding nozzle according to a first modification; FIG. 10 is a cross-sectional view showing a state that the air/water feeding nozzle has been fitted to the distal end portion, according to a second modification; and FIG. 11 is a perspective view partially showing the distal end portion to which the air/water feeding nozzle has been fitted, according to a third modification.

As shown in FIG. 1, an endoscope 1 is configured, being provided with an insertion portion 2 configured to be inserted into a subject, an operation portion 3 connectedly arranged on a proximal end side of the insertion portion 2, a universal cord 8 extended from the operation portion 3, and a connector 9 provided on an extension end of the universal cord 8.

Note that the endoscope 1 is electrically connected to a control apparatus, such as a video processor, and an external apparatus not shown, which is an illumination apparatus, via the connector 9.

The operation portion 3 is provided with an upward-and-downward bending operation knob 4 configured to cause a bending portion 12 of the insertion portion 2 to bend in upward and downward directions and a left-and-right bending operation knob 5 configured to cause the bending portion 12 to bend in left and right directions.

Furthermore, the operation portion 3 is provided with a fixing lever 6 configured to fix a rotational position of the upward-and-downward bending operation knob 4 and a fixing knob 7 configured to fix a rotational position of the left-and-right bending operation knob 5.

The insertion portion 2 is configured with a distal end portion 11, the bending portion 12 and a flexible tube portion 13 being connectedly arranged in that order from a distal end side and is elongatedly formed so as to be easily inserted into a subject.

The bending portion 12 is so as to, by being bent, for example, in four directions of upward, downward, left and right directions by a rotation operation of the upward-and-downward bending operation knob 4 and the left-and-right bending operation knob 5, change an observation direction of an image pickup unit not shown, which is provided inside the distal end portion 11, or improve insertability of the distal end portion 11 inside a subject.

As shown in FIG. 2, on a distal end face of a distal end cover 25 provided on the distal end portion 11, an observation lens 21 constituting an observation optical system, for example, a plurality of illumination lenses 22 and 22 constituting an illumination optical system, and an air/water feeding nozzle 23 as a fluid jet nozzle are provided, and an opening 24 of a treatment instrument channel from which a treatment instrument is guided out is formed.

Note that, as shown in FIG. 3, the distal end portion 11 of the insertion portion 2 has a distal end rigid portion 26 as a holding member configured to hold built-in components, and the distal end cover 25 described above is fixed to a distal end face of the distal end rigid portion 26 by adhesive or the like.

The distal end cover 25 provided on the distal end portion 11 is in a disc shape as an example and made of, for example, resin. The distal end cover 25 is provided with an observation optical system through-hole 31, illumination optical system through-holes 32, here, two illumination optical system through-holes 32, a nozzle through-hole 33 and a channel through-hole 34.

The observation lens 21 is fixedly arranged in the observation optical system through-hole 31 with watertightness retained, and the illumination lenses 22 are fixedly arranged in the illumination optical system through-holes 32 with watertightness retained. Further, the air/water feeding nozzle 23 is insertedly fitted in the nozzle through-hole 33 with watertightness retained.

Note that, in the present embodiment, cross-sectional shapes of the observation optical system through-hole 31, the nozzle through-hole 33 and the channel through-hole 34 are shown as circular shapes, and cross-sectional shapes of the two illumination optical system through-holes 32 are shown as rectangular shapes. Note that the cross-sectional shapes of the respective through-holes are not limited to the shapes but are appropriately set in accordance with shapes of members arranged in the through-holes.

The distal end rigid portion 26 is in a substantially cylindrical shape and is formed, for example, with rigid resin or metal.

In the distal end rigid portion 26, for example, an observation optical system holding hole 35 in which an observation optical unit (not shown) is to be insertedly fixed, illumination optical system holding holes 36, here two illumination optical system holding holes 36, in which an illumination optical unit (not shown) is to be insertedly fixed, a nozzle holding hole 37 in which the air/water feeding nozzle 23 is to be insertedly fixed, and a channel holding hole 38 in which a channel pipe sleeve (not shown) to be connected to the treatment instrument channel (not shown) is to be insertedly fixed are formed as through-holes to be a plurality of holes for holding a plurality of built-in components.

Note that the distal end rigid portion 26 is only required to be a rigid member, and it is not limited to resin or metal but may be made of ceramics or the like.

Here, a configuration of the air/water feeding nozzle 23 as a cylindrical member, which is a fixed member to be fixed to the distal end portion 11, will be described below in detail.

As shown in FIG. 4, the air/water feeding nozzle 23 is configured having a nozzle head 52 in which a fluid jet hole 51 is formed, and a substantially cylindrical barrel portion 53 which is extended from the nozzle head 52 and has a diameter smaller than that of the nozzle head 52.

The barrel portion 53 is configured having a sealing rubber 54 for watertight retention, such as an O-shaped ring, arranged on an upper end part so as to be in contact with the nozzle head 52, a V groove 55 which is a groove portion formed midway on a lower side of the sealing rubber 54, a flat portion 56 for positioning a direction of the fluid jet hole 51 of the nozzle head 52, which is formed so that so-called D-cut is obtained, a cylindrical portion 57 with a diameter slightly smaller than the diameter of a part where the V groove 55 and the flat portion 56 are formed, and a cylindrical sealing rubber 58 for watertight retention provided on a lower end of the cylindrical portion 57.

Note that two flat portions 56 are formed, here, in front and rear directions on a front side to be the fluid jet hole 51 side of the barrel portion 53 and a rear side on an opposite side of the front side so that two-side cut in a double D-cut shape is achieved. Further, the number of the flat portions 56 may be, of course, one.

Next, a part fixation structure of the endoscope, which is provided in the distal end rigid portion 26 and the distal end cover 25 to fix the air/water feeding nozzle 23 to the distal end portion 11, will be described below in detail.

As shown in FIG. 5, on a surface of the distal end rigid portion 26, a pin setting groove 42 as a first accommodating portion in a long hole shape for setting a pin 41 as an elastic member, which is, for example, a stainless-steel rod body, at a position of interfering with an outer circumferential portion of the nozzle holding hole 37 into which the air/water feeding nozzle 23 is to be insertedly fixed, by as little as 0.1 to 0.2 mm, and a pin relief groove 43 as a second accommodating portion as a pin relief portion communicating to a midway part of the pin setting groove 42 and formed in a concave shape with a longitudinal-direction length shorter than that of the pin setting groove 42 are formed.

Note that the pin setting groove 42 is formed so as to have a longitudinal axis in a direction orthogonal to a hole axis (not shown) of the nozzle holding hole 37.

Further, in the nozzle holding hole 37, hole flat portions 39 with which the two respective flat portions 56 of the air/water feeding nozzle 23 are to come into surface-contact and which are for positioning a direction of the fluid jet hole 51 of the nozzle head 52 when the air/water feeding nozzle 23 is insertedly fitted are formed such that they face each other.

As shown in FIG. 6, after the pin 41 is set in the pin setting groove 42, the distal end cover 25 is fastened to the distal end face of the distal end rigid portion 26. Note that, at this time, hole axes (not shown) of the nozzle through-hole 33 of the distal end cover 25 and the nozzle holding hole 37 of the distal end rigid portion 26 are in a state of substantially corresponding to each other.

In this state, the air/water feeding nozzle 23 is inserted from the barrel portion 53 side toward the nozzle through-hole 33 of the distal end cover 25. Note that the air/water feeding nozzle 23 is inserted, with the two flat portions 56 adjusted in a direction of being in surface-contact with the hole flat portions 39 of the nozzle holding hole 37, respectively.

Note that the air/water feeding nozzle 23 is structured so that, by the cylindrical portion 57 of the air/water feeding nozzle 23 coming into contact with the nozzle holding hole 37, the air/water feeding nozzle 23 and the nozzle holding hole 37 are positioned on a same axis.

At this time, the pin 41 comes into contact with an outer circumferential portion of the air/water feeding nozzle 23, bends by being pressed in an outer diameter direction of the air/water feeding nozzle 23 and enters the pin relief groove 43 as shown in FIG. 7. That is, the pin 41 is configured to, by entering the pin relief groove 43 with a length shorter than that of the pin setting groove 42, be in a state that both end parts are pressed, elastically deform, bend and play a role of a spring by restoring force of trying to return to an original state.

Then, the air/water feeding nozzle 23 is inserted until an end face portion 52a constituting an outward flange of the nozzle head 52 comes into contact with a stepped portion 33a constituting an inward flange formed in the nozzle through-hole 33 of the distal end cover 25.

Further, at same time when the air/water feeding nozzle 23 is inserted into the nozzle through-hole 33 until the end face portion 52a comes into contact, and stops, the pin 41 is engageably inserted into the V groove 55.

Note that, when falling into the V groove 55 which the pin 41 is to be engageably inserted, the pin 41 comes into contact with a slope of the V groove 55 and adds a force component of pressing the air/water feeding nozzle 23 in a depth (insertion) direction of the nozzle holding hole 37.

Therefore, the air/water feeding nozzle 23 is fitted without backlash, holding the state of the end face portion 52a being in contact with the stepped portion 33a of the distal end cover 25.

That is, the pin 41 is set to keep the air/water feeding nozzle 23 at a fitted position without backlash and set to such predetermined required strength that the air/water feeding nozzle 23 does not come out, for example, set so as to withstand tensile strength of 1 kg.

Note that the air/water feeding nozzle 23 is configured so that, when being pulled with the predetermined required strength, for example, an amount of force of 1 kg or more, the pin 41 comes out from the V groove 55, bends by elastic deformation and enters the pin relief groove 43, and the air/water feeding nozzle 23 comes out from the nozzle holding hole 37.

Note that, though description has been made above on the structure for fixing the air/water feeding nozzle 23 to the distal end portion 11 as an example, the technique is also applicable to a component attached to and detached from the distal end portion 11.

Thus, though description has been made on the air/water feeding nozzle 23 as an example here, the endoscope 1 of the present embodiment is structured so as to fix a cylindrical member, such as the illumination unit and the image pickup unit attached to and detached from the distal end portion 11 of the insertion portion 2, to the distal end portion 11 with predetermined required strength by elastic deformation of the pin 41, without using a screw member.

Thereby, the endoscope 1 makes it possible to, when attaching or detaching a cylindrical member to or from the distal end portion 11, easily attach or detach the cylindrical member in a single operation without damaging the distal end cover 25 or the distal end rigid portion 26 and makes it possible to prevent cost of repair, maintenance and the like from increasing.

Furthermore, by forming the first accommodating portion and the second accommodating portion on the surface of the distal end rigid portion 26, it is possible to improve workability of the distal end rigid portion 26.

According to the above description, the endoscope 1 of the present embodiment can be configured to reduce the cost of repair, maintenance and the like without damaging the distal end cover 25 and the distal end rigid portion 26 and make it possible to easily attach and detach a part to be fitted to the distal end portion 11 in a single operation.

(First Modification)

As shown in FIG. 9, the V groove 55 formed on the air/water feeding nozzle 23 may be formed only at a position facing the pin 41.

(Second Modification)

As shown in FIG. 10, a pin setting groove 44 and a pin relief groove 45 may be also formed on a back surface of the distal end cover 25 similarly to the surface of the distal end rigid portion 26.

Note that the pin setting groove 44 and the pin relief groove 45 of the distal end cover 25 are formed at positions facing the pin setting groove 42 and the pin relief groove 43 of the distal end rigid portion 26 in a state that the distal end cover 25 is fitted to the distal end rigid portion 26.

The pin setting grooves 42 and 44 and the pin relief grooves 43 and 45 are formed with short depth-direction dimensions because it is sufficient if the pin 41 can be accommodated in space in a state that the pin setting grooves 42 and 44 overlap each other.

(Third Modification)

As shown in FIG. 11, a lateral hole 47 communicating to the pin setting groove 42 for inserting the pin 41 may be formed in the distal end rigid portion 26.

Note that the lateral hole 47 is formed so that one end opens on an outer circumferential portion of the distal end rigid portion 26, and the other end opens on one end face of the pin setting groove 42; and it is possible to insert or pull out the pin 41 even after the distal end cover 25 is fitted to the distal end rigid portion 26.

Furthermore, the air/water feeding nozzle 23 may obtain watertightness between the air/water feeding nozzle 23 and the distal end cover 25/the distal end rigid portion 26 by adhesive such as epoxy resin and silicone resins without being provided with the sealing rubbers 54 and 58 for watertight retention, though this is not shown.

Further, both end parts of the pin 41 may be released in the state that the pin 41 is accommodated in the pin setting groove 42 so that a degree of spring in a state of both ends being supported may be adjusted.

(First Reference Example)

Figure 12:
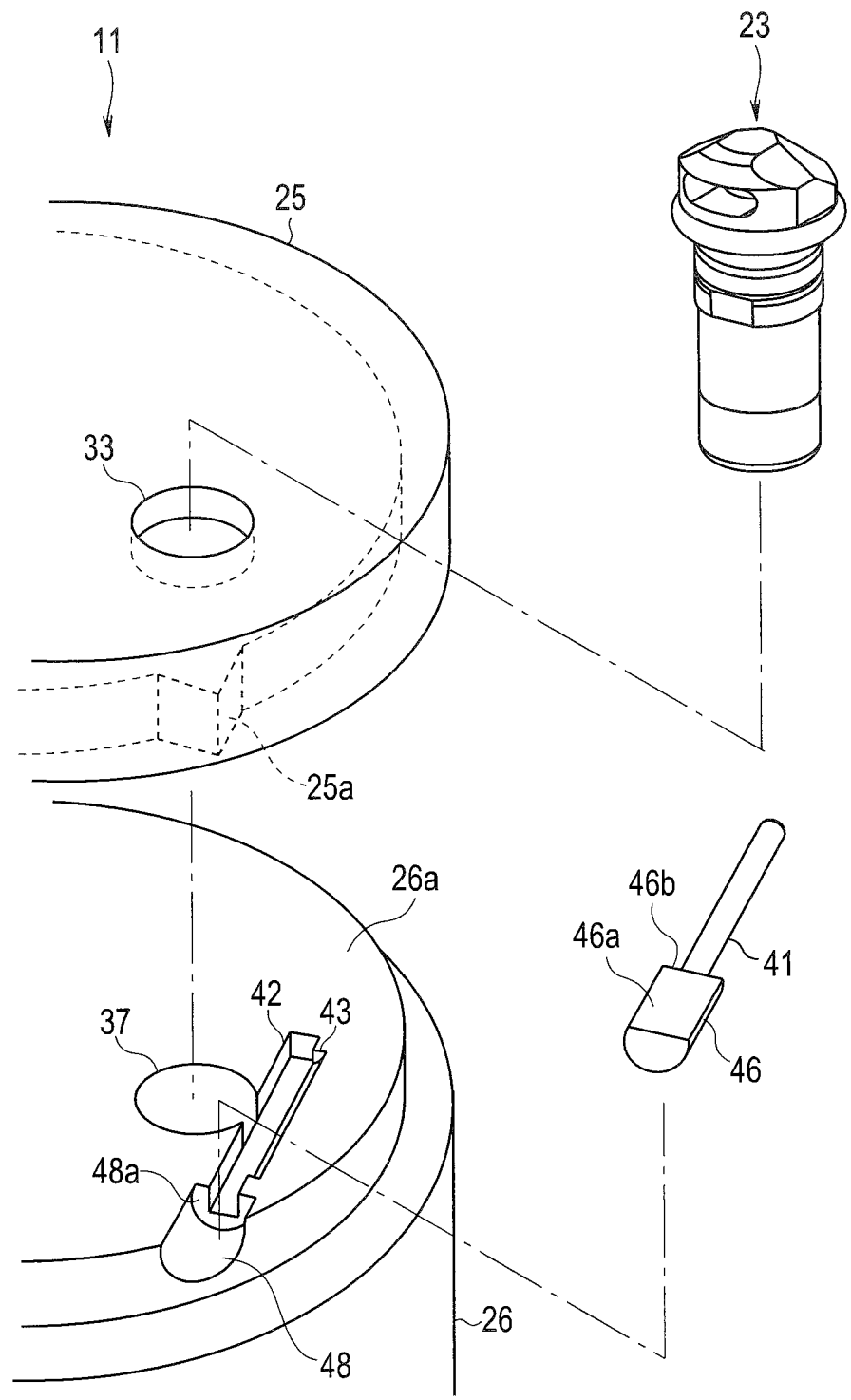
FIG. 12 is a perspective view partially showing the distal end portion to which the air/water feeding nozzle has been fitted, according to a first reference example of the aspect of the present invention.
Figure 13:
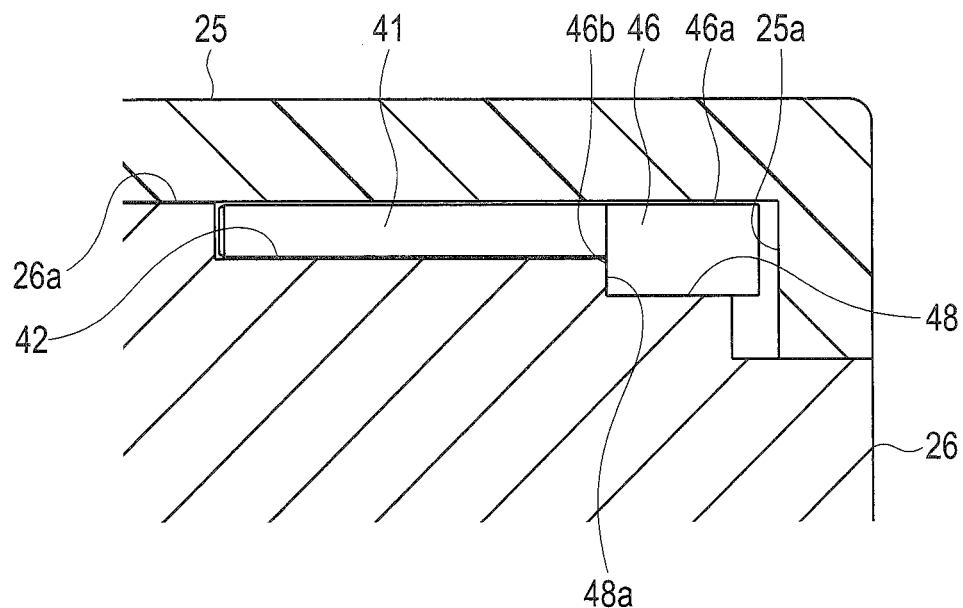
FIG. 13 is a cross-sectional view showing a state that the pin for fixing the air/water feeding nozzle to the distal end portion is inserted, according to the first reference example of the aspect of the present invention.

FIG. 12 is a perspective view partially showing the distal end portion to which the air/water feeding nozzle has been fitted. FIG. 13 is a cross-sectional view showing a state that the pin for fixing the air/water feeding nozzle to the distal end portion is inserted.

By the way, in the embodiment described above, the pin relief groove 43 is provided as space where the pin 41 for fixing the nozzle bends in order that the air/water feeding nozzle 23 can be attached or detached at time of repair, assembly and the like. However, in a process for bonding the distal end rigid portion 26 and the distal end cover 25, it is necessary to prevent adhesive from flowing into the pin relief groove 43 in order to secure space where the pin 41 inserted in the pin setting groove 42 certainly bends.

It is difficult, however, to block the adhesive flowing in from an outer circumferential side of the distal end rigid portion 26 by the pin 41 in a straight round rod shape.

Therefore, in the present reference example, a configuration is adopted in which a projecting portion 46 with a D-cut-shaped cross section is provided on one end portion of the pin 41 as shown in FIG. 12.

More specifically, an outer diameter of the projecting portion 46 projects much more than that of the pin 41, and a flat portion 46a with a D-cut-shaped cross section is formed on a part of the projecting portion 46, at a position on a same plane as the outer diameter of the pin 41.

Further, the distal end rigid portion 26 is provided with an accommodating groove 48 to accommodate the projecting portion 46 of the pin 41, which is formed in a concave shape up to the outer circumferential portion so as to communicate to the pin setting groove 42.

Furthermore, in an internal surface of the distal end cover 25, a recess-shaped hole portion 25a configured to accommodate the projecting portion 46 of the pin 41 projecting from the outer circumferential portion of the distal end rigid portion 26 is formed.

In the endoscope 1 of the present modification configured as described above, when the pin 41 is set in the pin setting groove 42, the flat portion 46a of the projecting portion 46 is caused to be accommodated in the accommodating groove 48 so that the flat portion 46a of the projecting portion 46 is aligned with a distal end face 26a of the distal end rigid portion 26.

At this time, the projecting portion 46 is accommodated so that a projecting face 46b on an extension side of the round-rod-shaped pin 41 comes into contact with an end face 48a of the accommodating groove 48. Then, the distal end cover 25 is bondedly fixed to the distal end rigid portion 26.

In this state, an internal surface 25b of the distal end cover 25 comes into contact with the distal end face 26a of the distal end rigid portion 26 and the flat portion 46a of the projecting portion 46.

Thus, entry of adhesive into the pin setting groove 42 from the distal end face 26a side of the distal end rigid portion 26 is prevented by the distal end cover 25, and entry of the adhesive from an outer circumferential direction of the distal end rigid portion 26 is prevented by contact between the projecting face 46b of the projecting portion 46 and the end face 48a of the accommodating groove 48.

Due to such a configuration, it is possible to, in the process for bonding the distal end cover 25 to the distal end rigid portion 26, prevent the adhesive from flowing into the pin setting groove 42 from both of a longitudinal axis direction of the distal end portion 11 provided on the insertion portion 2 of the endoscope 1 and a lateral axis direction, which is a diameter direction, and prevent the adhesive from flowing into the pin relief groove 43.

As a result, in the endoscope 1, the pin relief groove 43 can be prevented from being filled with the adhesive, and the space where the pin 41 bends can be secured. Therefore, it is possible to attach or detach the air/water feeding nozzle 23 to or from the distal end portion 11 at time of repair, assembly and the like.

Note that the cross section of the projecting portion 46 is not limited to the D-cut-shaped cross section but may be in a rectangular shape, a round rod shape or the like. Further, the stepped portion formed between the projecting portion 46 and the pin 41 in a straight round rod shape may be in a tapered shape.

(Second Reference Example)

Figure 14:
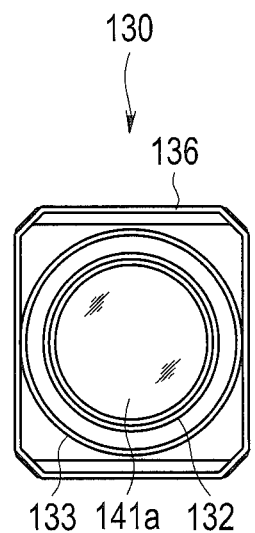
FIG. 14 is a side view of an image pickup unit according to a second reference example of the aspect of the present invention.
Figure 15:
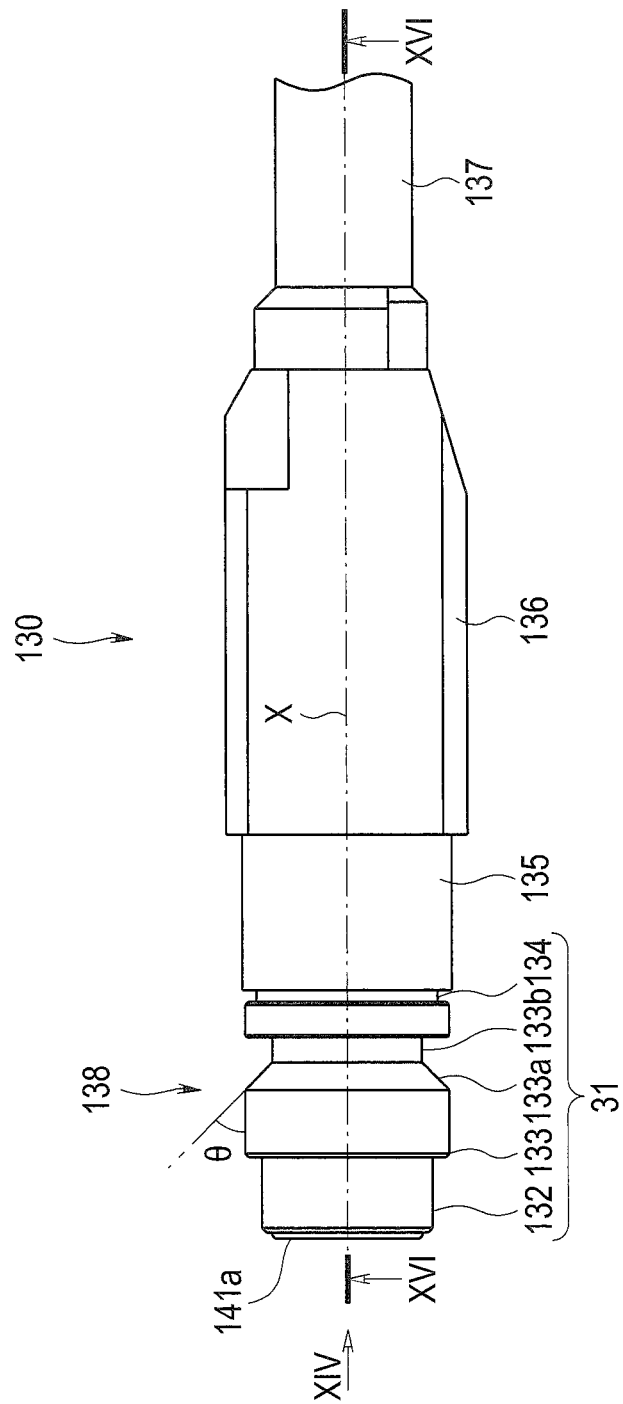
FIG. 15 is a front view of an arrow XIV of the image pickup unit of FIG. 14 according to the second reference example of the aspect of the present invention.
Figure 16:
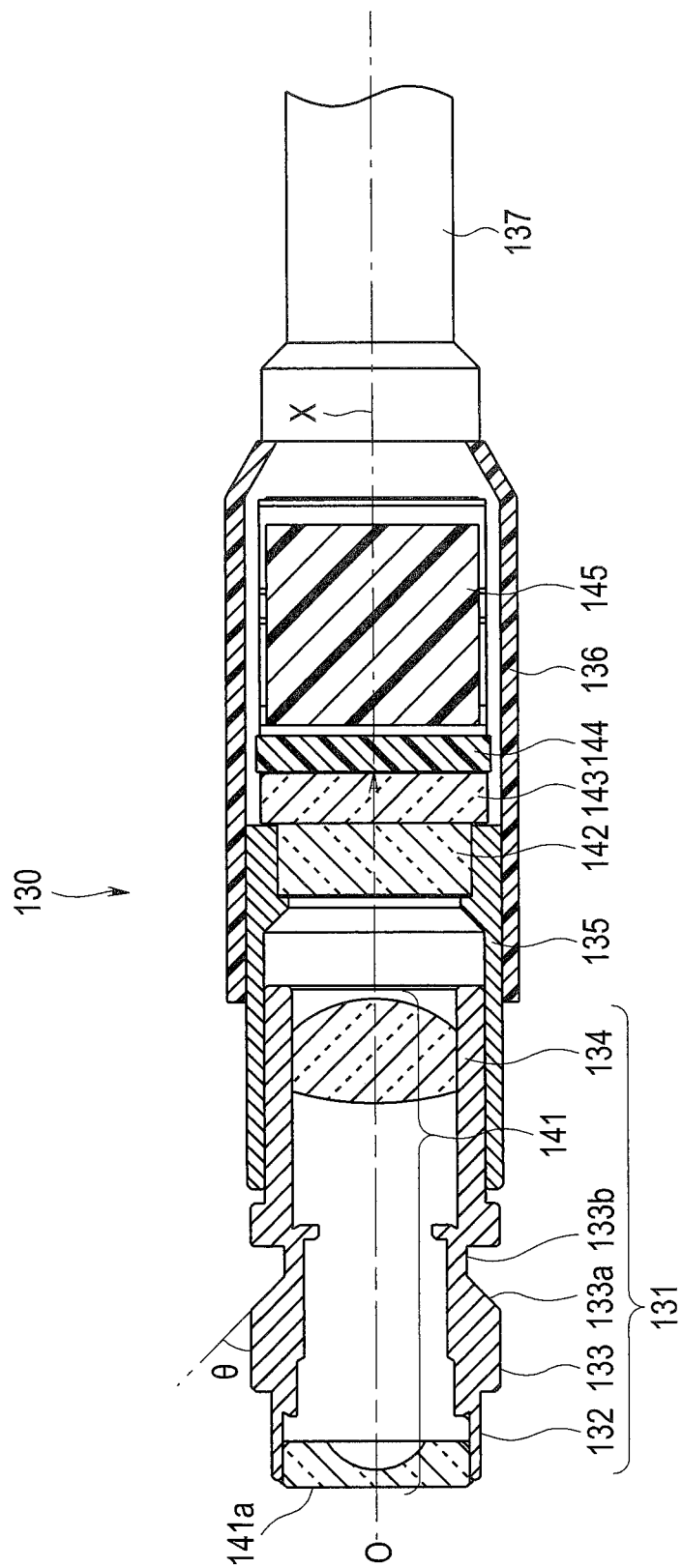
FIG. 16 is a XVI-XVI line sectional view of the image pickup unit of FIG. 15 according to the second reference example of the aspect of the present invention.
Figure 17:
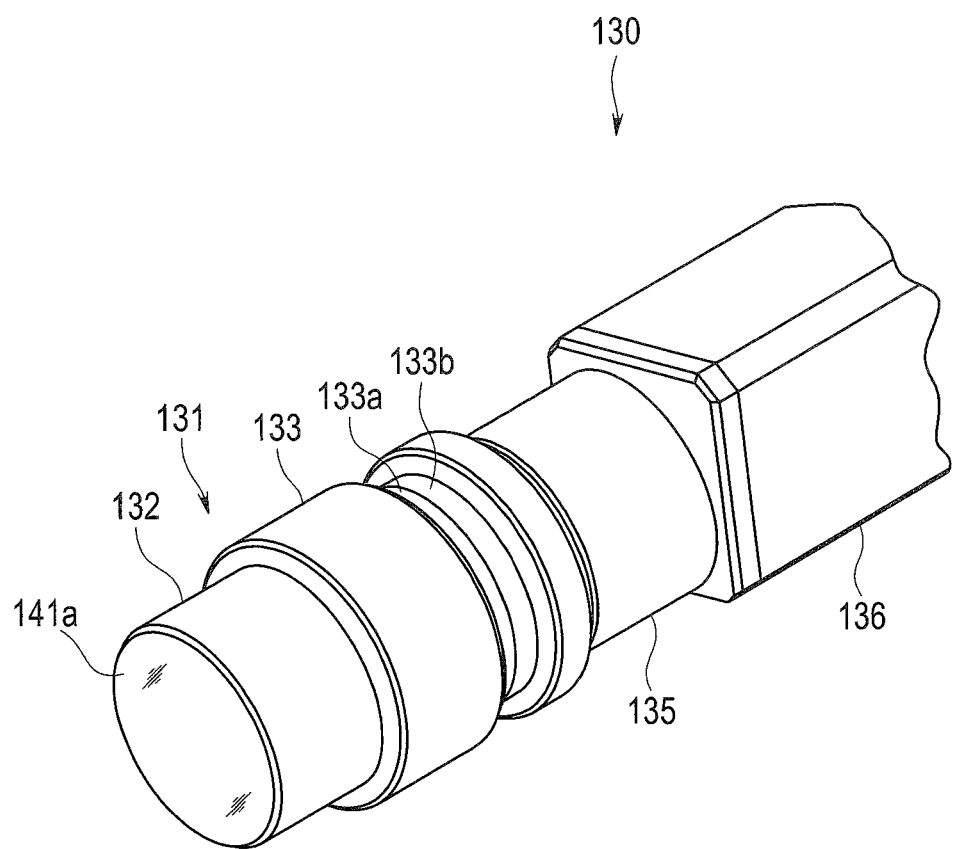
FIG. 17 is a perspective view showing a distal end part of the image pickup unit according to the second reference example of the aspect of the present invention.
Figure 18:
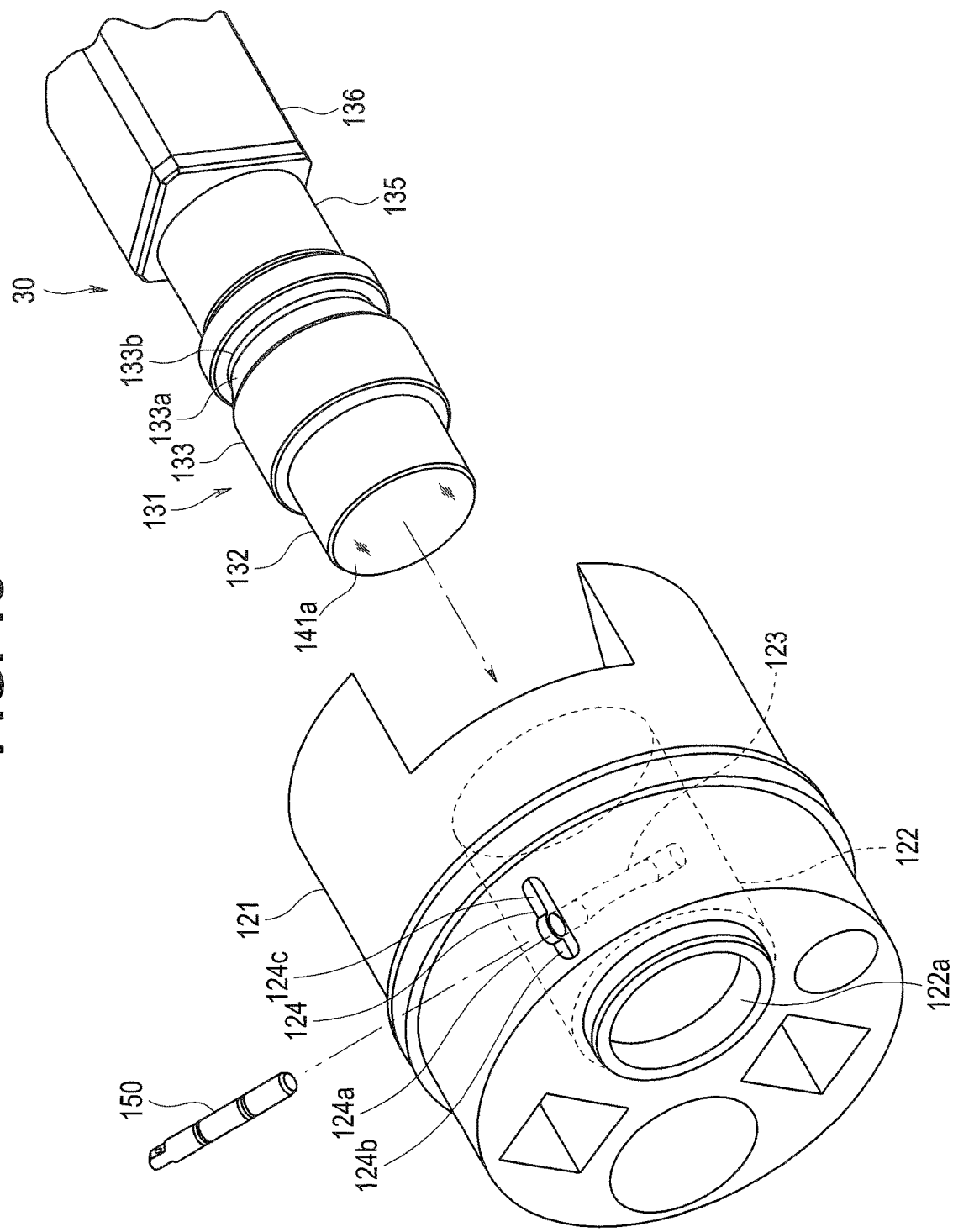
FIG. 18 is an exploded perspective view showing a state of fitting the image pickup unit to the distal end rigid portion, according to the second reference example of the aspect of the present invention.
Figure 19:
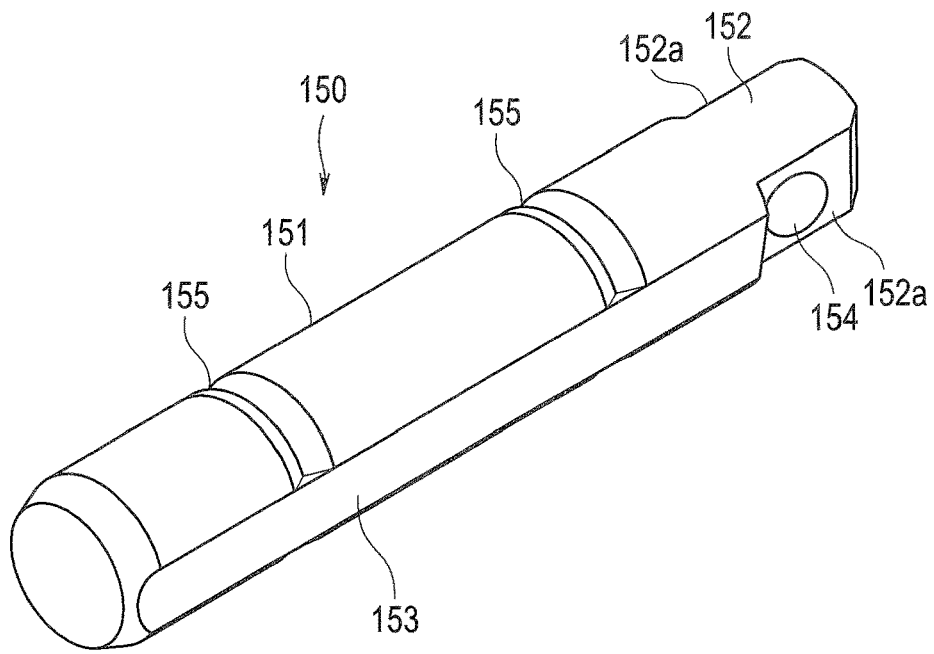
FIG. 19 is a perspective view showing a configuration of the fixing pin according to the second reference example of the aspect of the present invention.
Figure 20:
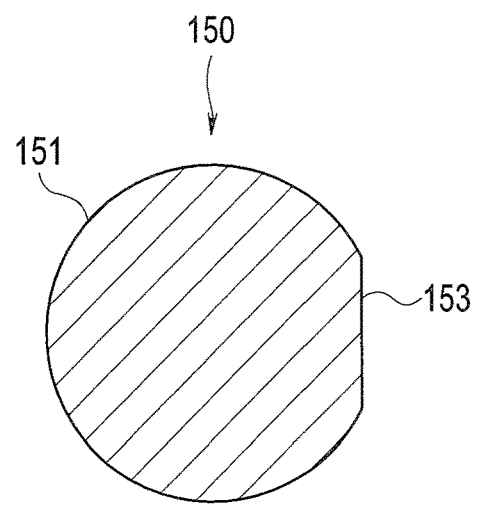
FIG. 20 is a cross-sectional view showing the configuration of the fixing pin according to the second reference example of the aspect of the present invention.
Figure 21:
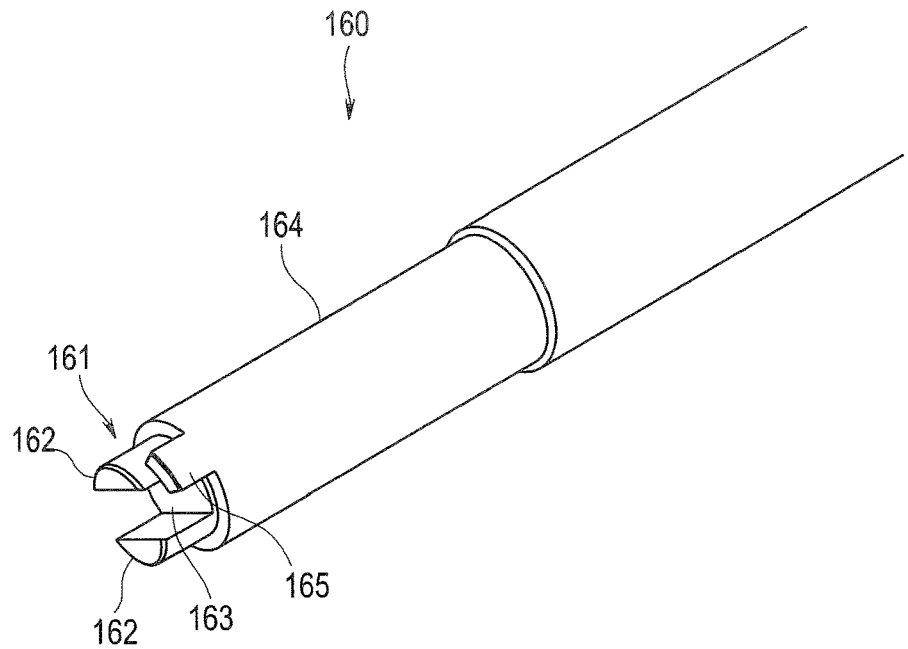
FIG. 21 is a perspective view showing a configuration of a jig according to the second reference example of the aspect of the present invention.
Figure 22:
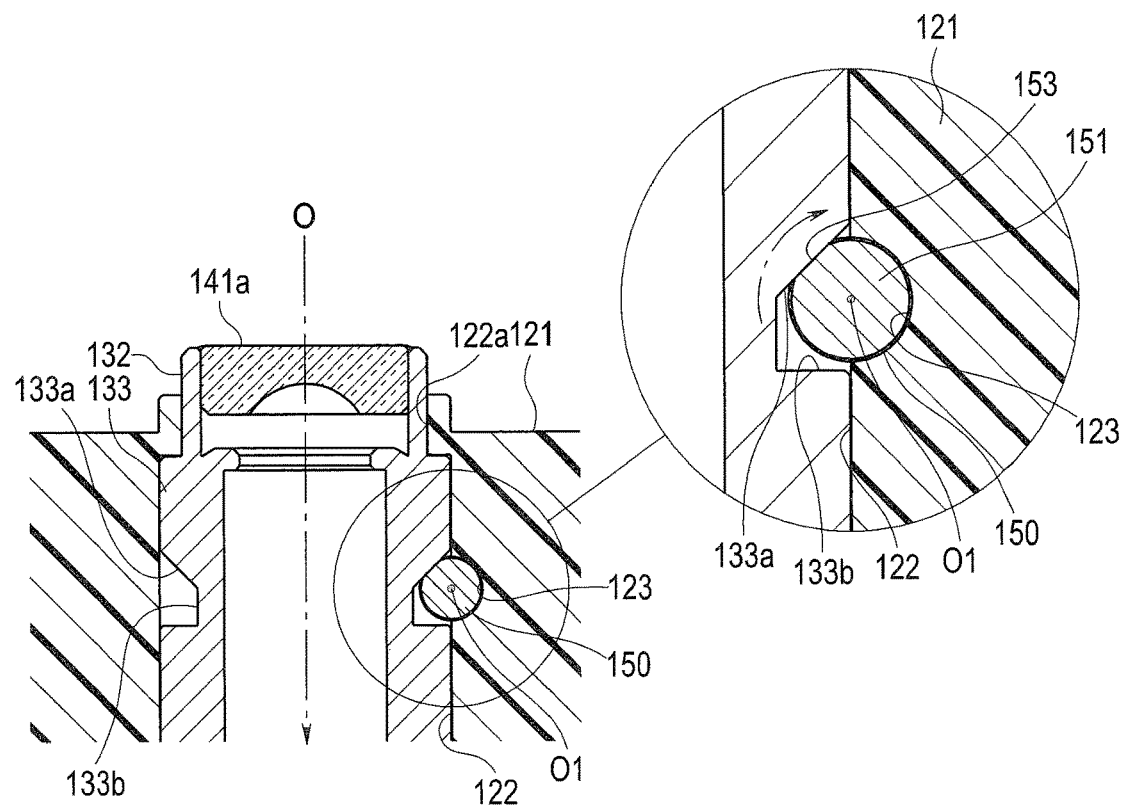
FIG. 22 is a partial sectional view showing a state that the fixing pin to be fixed to the image pickup unit is inserted in the distal end constituting portion, according to the second reference example of the aspect of the present invention.
Figure 23:
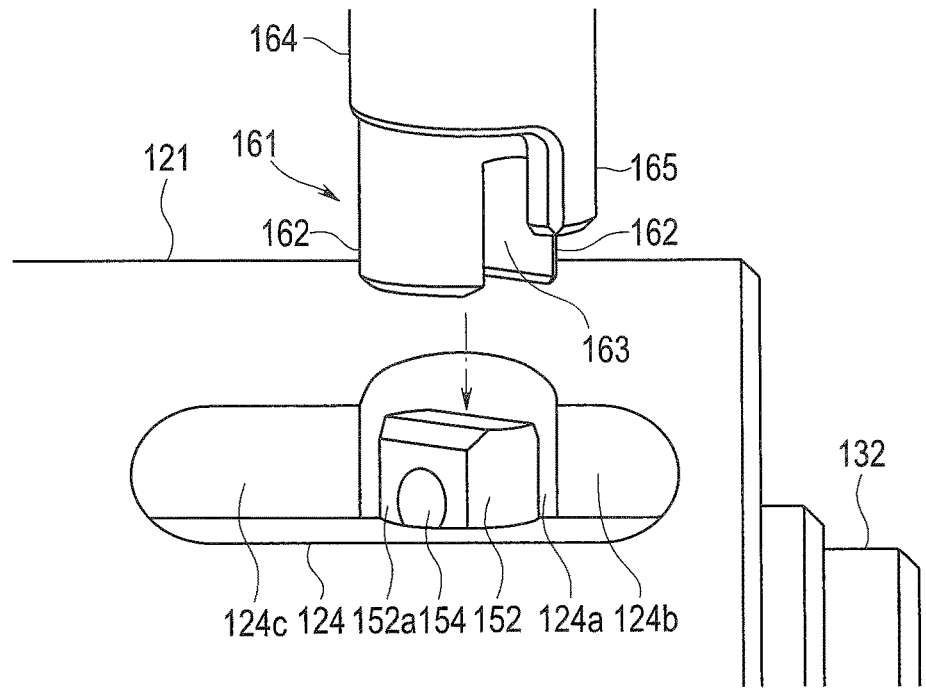
FIG. 23 is a perspective view showing a state before a head portion of the fixing pin projecting from a stepped portion of the distal end constituting portion is rotated by the jig, according to the second reference example of the aspect of the present invention.
Figure 24:
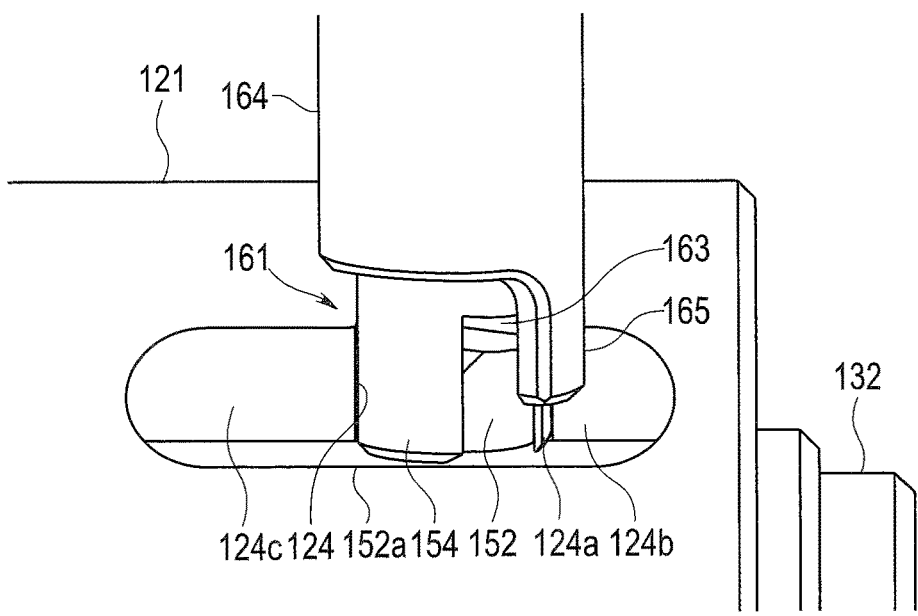
FIG. 24 is a perspective view showing a state that the jig is fitted over the head portion of the fixing pin, according to the second reference example of the aspect of the present invention.
Figure 25:
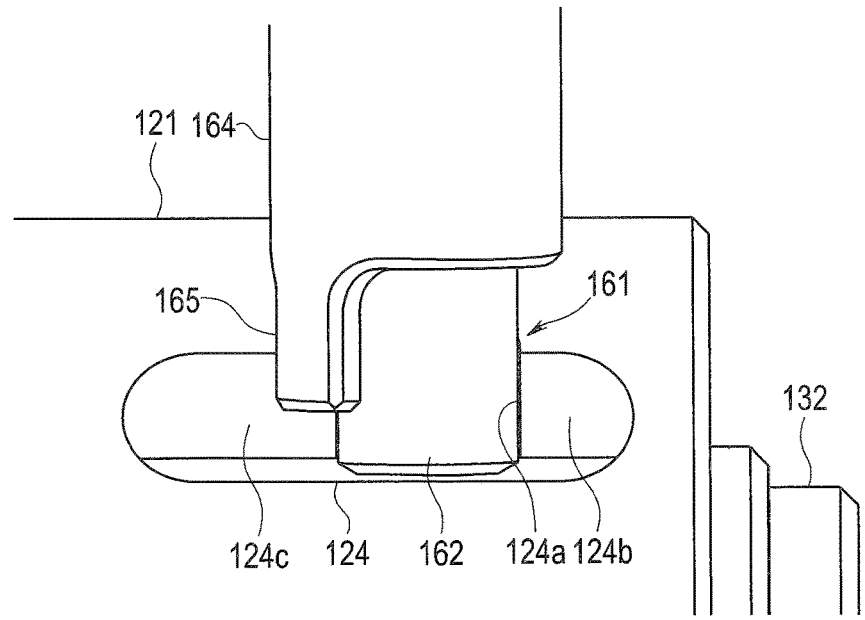
FIG. 25 is a perspective view showing a state that the fixing pin has been rotated by the jig, according to the second reference example of the aspect of the present invention.
Figure 26:
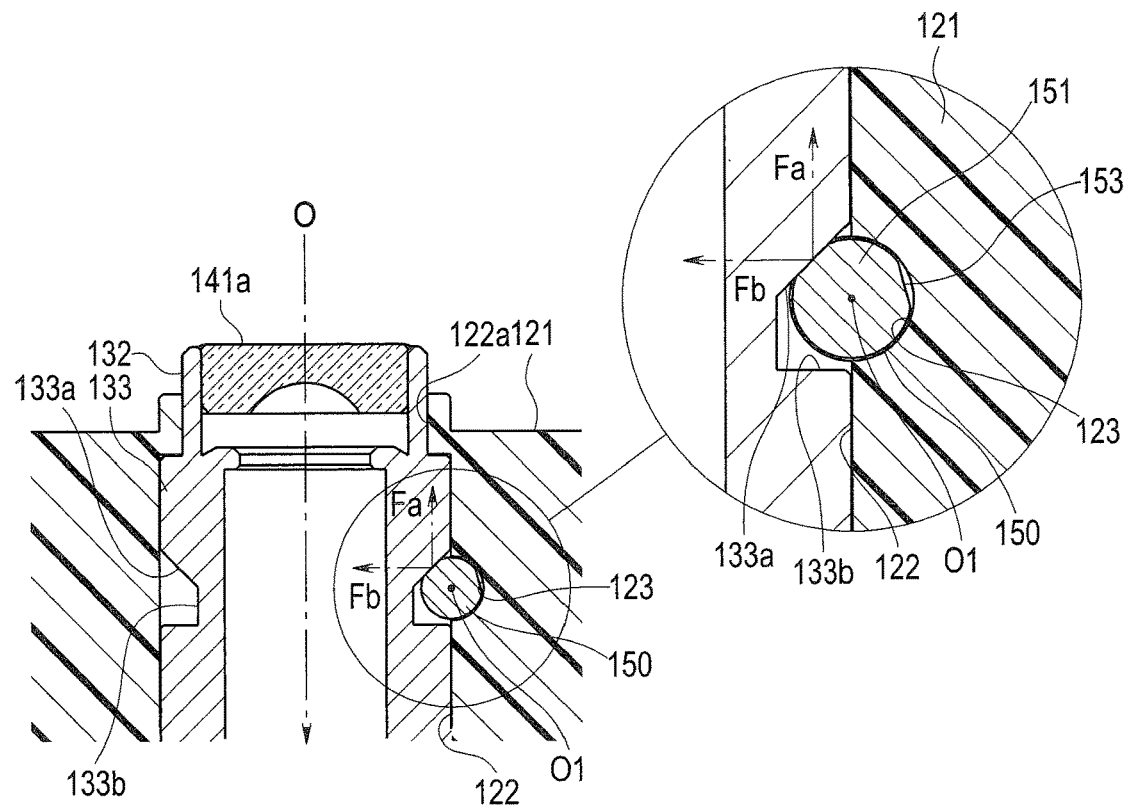
FIG. 26 is a partial sectional view showing a state that the fixing pin has been rotated, and the image pickup unit is fixed to the distal end constituting portion, according to the second reference example of the aspect of the present invention.
Figure 27:
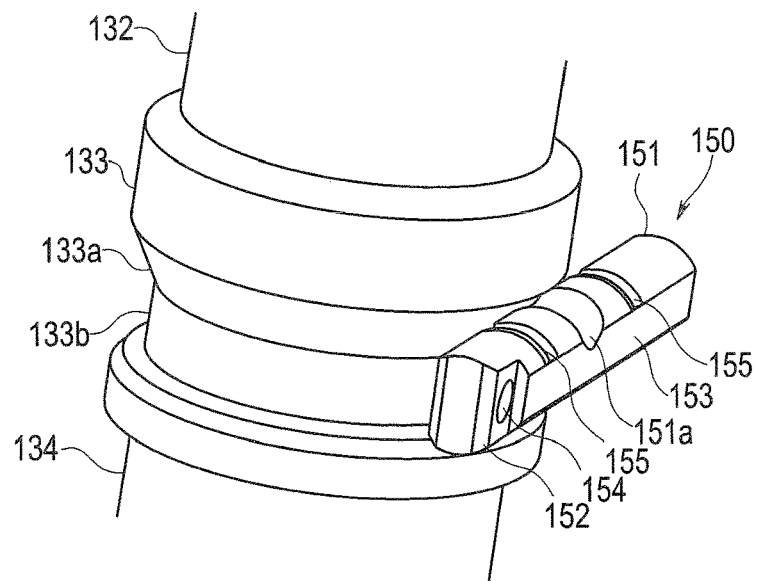
FIG. 27 is a perspective view showing a state that the image pickup unit is fixed with the fixing pin, according to the second reference example of the aspect of the present invention.
Figure 28:
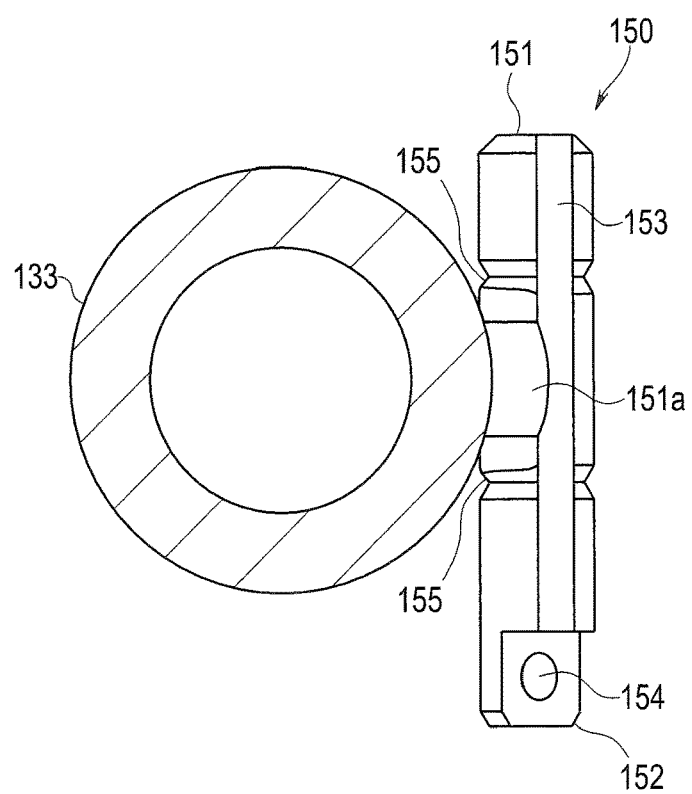
FIG. 28 is a cross-sectional view showing a state that the image pickup unit is fixed with the fixing pin, according to the second reference example of the aspect of the present invention.

FIG. 14 is a side view of an image pickup unit; FIG. 15 is a front view of an arrow XIV of the image pickup unit of FIG. 14; FIG. 16 is a XVI-XVI line sectional view of the image pickup unit of FIG. 15; FIG. 17 is a perspective view showing a distal end part of the image pickup unit; FIG. 18 is an exploded perspective view showing a state of fitting the image pickup unit to the distal end rigid portion; FIG. 19 is a perspective view showing a configuration of the fixing pin; FIG. 20 is a cross-sectional view showing the configuration of the fixing pin; FIG. 21 is a perspective view showing a configuration of a jig; FIG. 22 is a partial sectional view showing a state that the fixing pin to be fixed to the image pickup unit is inserted in the distal end constituting portion; FIG. 23 is a perspective view showing a state before a head portion of the fixing pin projecting from a stepped portion of the distal end constituting portion is rotated by the jig; FIG. 24 is a perspective view showing a state that the jig is fitted over the head portion of the fixing pin; FIG. 25 is a perspective view showing a state that the fixing pin has been rotated by the jig; FIG. 26 is a partial sectional view showing a state that the fixing pin has been rotated, and the image pickup unit is fixed to the distal end constituting portion; FIG. 27 is a perspective view showing a state that the image pickup unit is fixed with the fixing pin; and FIG. 28 is a cross-sectional view showing a state that the image pickup unit is fixed with the fixing pin.

Apart from the configuration in which the air/water feeding nozzle 23 is detachably fixed to the distal end portion 11 as in the embodiment and modifications described above, description will be made on an example of fixing an image pickup apparatus to the distal end portion 11.

For example, such a form is known that, in a configuration in which an image pickup apparatus is fixed to the distal end rigid portion 26 as a frame member which is a holding member, a D-cut pin member is fittedly fixed by being rotated and deformed.

In such a configuration, if a direction in which the pin member deforms is changeable when the pin member is rotated and fixed, variation occurs in a range in which the pin member is in contact with the image pickup apparatus, and variation also occurs in fixation force of fixing the image pickup apparatus to the distal end rigid portion 26.

Accordingly, a configuration of the present modification will be described below in detail.

The distal end portion 11 of the insertion portion 2 of the endoscope 1 has a built-in endoscope image pickup unit (hereinafter simply referred to as an image pickup unit) 130 shown in FIGS. 14 to 17.

As shown in FIGS. 14 to 16, the image pickup unit 130 has an objective lens unit 138, an image pickup device holding frame 135 and a reinforcing frame 136, and an image pickup cable 137 extends from a proximal end of the reinforcing frame 136.

The objective lens unit 138 has a substantially tubular lens frame 131. In rear of the lens frame 131, the image pickup device holding frame 135 is fitted. In rear of the image pickup device holding frame 135, the reinforcing frame 136 is fitted.

The lens frame 131 is here made of metal such as stainless steel. As shown in FIG. 16, the lens frame 131 is a lens fixing frame configured to hold an objective lens group 141, which is an objective optical system, and is configured having an observation window holding portion 132, a barrel portion 133 in an outward flange shape, with a diameter of its outer circumferential part increased larger than the observation window holding portion 132, and a fitted portion 134 which is arranged being connected to the barrel portion 133 and which is fitted by a distal end part of the image pickup device holding frame 135 being fitted over the fitted portion 134, in that order from a distal end side.

The observation window holding portion 132 of the lens frame 131 holds an objective lens 141a which is arranged on a most distal end side of the objective lens group 141 and which is to be an observation window (see FIGS. 15 and 16). As shown in FIGS. 14, 16 and 17, a circumferential groove 133b in which a slope portion 133a as a contact surface is formed in a circumferential direction on the distal end side is formed on the barrel portion 133 of the lens frame 131.

As shown in FIGS. 14 and 16, the slope portion 133a here is a partial conical surface which inclines at a predetermined acute angle θ, for example 45° (θ=45°) in an internal diameter direction toward a proximal end side, relative to a front-and-back direction of the image pickup unit 130.

That is, the circumferential groove 133b is in such a shape that the acute-angle slope portion 133a having the predetermined angle θ, for example, 45° relative to a longitudinal axis X (see FIG. 15) along the front-and-back direction of the image pickup unit 130 is formed on the distal end side so as to incline in the inner diameter direction toward the proximal end side. Note that the slope portion 133a is not limited to a straight cross section but may be a convex curved surface or a concave curved surface.

The image pickup device holding frame 135 of the lens frame 131 holds an optical member 142 at a proximal end portion (see FIG. 16). A front face of cover glass 143 is fastened to a rear face of the optical member 142 by optical adhesive. A solid image pickup device 144, which is image pickup means such as a CCD and a CMOS, is fastened to a rear face of the cover glass by optical adhesive.

The solid image pickup device 144 is electrically connected to an image pickup substrate 145. The optical member 142 held by the image pickup device holding frame 135, the solid image pickup device 144 and the image pickup substrate 145 are covered with the reinforcing frame 136. The solid image pickup device 144 and the image pickup substrate 145 are surrounded by and covered with filler (not shown) such as adhesive inside the reinforcing frame 136 for purpose of moisture proofing, insulation and the like.

The image pickup unit 130 configured as described above is adapted so that a photographing light (an object image) of an optical axis O (see FIG. 16) incident on the objective lens group 141 is formed on a light receiving portion of the solid image pickup device 144. The solid image pickup device 144 photoelectrically converts the photographing light and outputs image pickup data of an object to the image pickup substrate 145.

Then, the image pickup substrate 145 electrically processes the image pickup data appropriately and outputs the image pickup data to an electrically connected communication cable (not shown). The communication cable is insertedly arranged in the endoscope 1 and is electrically connected to a video processor not shown, which is an external apparatus, via an electrical connector not shown, which is connected to the connector 9 shown in FIG. 1.

By the way, the distal end portion 11 of the insertion portion 2 is provided with a distal end constituting portion 121 as a distal end portion body which is a substantially cylindrical block made of synthetic resin here, similar to the distal end rigid portion 26 described above, shown in FIG. 18. A unit setting hole portion 122 into which the image pickup unit 130, which is a functional member here, is to be inserted is formed in the distal end constituting portion 121, and an observation hole portion 122a into which the observation window holding portion 132 of the image pickup unit 130 is to be inserted is provided on a distal end side of the unit setting hole portion 122.

Then, the image pickup unit 130 is inserted into the unit setting hole portion 122 from the proximal end side and insertedly fixed so that a state is obtained that a front face of the barrel portion 133 projecting in an outer diameter direction is in contact with a rear end face of the distal end constituting portion 121 which is steppedly formed, being positioned at a rear end of the observation hole portion 122a, and forms the unit setting hole portion 122.

Here, a part fixation structure of the endoscope 1 for fixing the image pickup unit 130 to the distal end constituting portion 121 provided on the distal end portion 11 will be described below in detail.

On one side periphery of the distal end constituting portion 121 to be a first fixed member here, a unit fixing hole portion 123 made with its midway part communicated to the unit setting hole portion 122 is formed toward an internal diameter direction of the distal end constituting portion 121 so as to correspond to a position where the slope portion 133a of the barrel portion 133 is arranged when the image pickup unit 130 to be a second fixed member here is fitted.

Note that the unit fixing hole portion 123 is orthogonal to the longitudinal axis X of the image pickup unit 130 when the image pickup unit 130 is fitted, and is formed on the distal end constituting portion 121 in a tangential direction relative to an outer circumferential portion of the lens frame 131.

In other words, the unit fixing hole portion 123 is formed so as to have an hole axis which is orthogonal to a hole axis of the unit setting hole portion 122 and is in the tangential direction relative to the slope portion 133a of the image pickup unit 130 arranged in the unit setting hole portion 122.

On the distal end constituting portion 121, such a stepped portion 124 that its cross section forms an L shape along the longitudinal direction is formed on an outer circumferential part where an opening of the unit fixing hole portion 123 is formed. On the stepped portion 124, a circular-arc concave portion 124a with a radius of curvature larger than that of the unit fixing hole portion 123 and wall face portions 124b and 124c along the longitudinal direction in front and back directions of the concave portion 124a.

A fixing pin 150 as a fixing member for fixing the image pickup unit 130 to the distal end constituting portion 121 is inserted in the unit fixing hole portion 123 formed in the distal end constituting portion 121. That is, the image pickup unit 130 and the distal end constituting portion 121 constitute fixed members fixed to each other by the fixing pin 150.

Note that the fixing pin 150 here is formed with metal softer than the metal (stainless steel) used for the lens frame 131 of the image pickup unit 130, for example, metal such as a kind of stainless steel with a lower hardness than the kind of the stainless steel used for the lens frame 131 and phosphor bronze.

As shown in FIGS. 19 and 20, the fixing pin 150 has a pin body 151 and a head portion 152 formed on one end of the pin body 151. On the pin body 151, a D-cut face is formed so that a cylindrical rod body has a D-shaped cross section, and a flat portion 153 as a non-contact portion is formed on a part of an outer circumference along a longitudinal axis direction.

Note that two or more flat portions 153, which are D-cut faces, may be formed, and an angle the respective flat portions 153 form may be arbitrarily set. Further, the flat portion 153 may not cover the entire length of the outer circumference along the longitudinal axis direction of the pin body 151. The flat portion 153 is only required to be formed at least from a position at which the fixing pin 150 comes into contact with the slope portion 133a of the barrel portion 133 of the image pickup unit 130 when being inserted into the unit fixing hole portion 123 up to the other end of the pin body 151.

Furthermore, the fixing pin 150 is provided with two circumferential grooves 155 having a V-shaped cross section at positions separate from each other by a predetermined distance along an axial direction.

Note that two flat portions 152a parallel to each other having a predetermined width are formed on the head portion 152, and the head portion 152 has a hole portion 154 made so as to pass through between the two flat portions 152a. Note that the fixing pin 150 here is a member replaced at each time of use (disposable).

Note that the two flat portions 152a may not be parallel to each other. An angle formed by the two flat portions 152a may be arbitrarily set.

Further, a predetermined axial rotation direction is specified for the unit fixing hole portion 123, and the fixing pin 150 is rotated to fix the image pickup unit 130 to the distal end constituting portion 121 after being inserted. At this time, a jig 160 as shown in FIG. 21 is used to rotate the fixing pin 150.

The jig 160 is provided with a recess portion 163 on a distal end portion 161, which forms two arm portions 162 so as to have two faces facing each other. Further, on the jig 160, a cylindrical body 164 having a large diameter is fixed, being fitted over the distal end portion 161, and the jig 160 has a projecting portion 165 extended from a part of a distal end of the cylindrical body 164.

The jig 160 configured as described above is used at time of rotating the fixing pin 150 around the axis by the head portion 152 of the fixing pin 150 being engageably inserted into the recess portion 163 so that the facing faces of the two arm portions 162 come into surface-contact with the flat portions 152a of the head portion 152.

Here, a configuration for fixing the image pickup unit 130 to the distal end constituting portion 121 in the endoscope 1 will be described below in detail.

First, the observation window holding portion 132 side of the lens frame 131 of the image pickup unit 130 to be the distal end side is insertedly fitted into the unit setting hole portion 122 from a rear end side of the distal end constituting portion 121 (see FIG. 18).

Then, the observation window holding portion 132 of the image pickup unit 130 is inserted into the observation hole portion 122a, and the front face of the barrel portion 133 is caused to come into contact with an end face of the distal end constituting portion 121 forming the unit setting hole portion 122.

After that, the image pickup unit 130 is rotated and adjusted to a predetermined position set in advance according to a direction (the upward, downward, left or right direction) of a photographing image to be acquired, relative to the distal end constituting portion 121.

The circumferential groove 133b formed on the barrel portion 133 of the image pickup unit 130 arranged inside the unit setting hole portion 122 in this way is positioned at the midway part of the unit fixing hole portion 123. At this time, the slope portion 133a formed on the distal end side of the circumferential groove 133b is in a state of being positioned inside the midway part of the unit fixing hole portion 123, inside the unit setting hole portion 122.

In this state, the fixing pin 150 is inserted into the unit fixing hole portion 123 of the distal end constituting portion 121 from the pin body 151 side. At this time, the pin body 151 of the fixing pin 150 is inserted into the unit fixing hole portion 123, with an axial rotation position adjusted so that the flat portion 153 contactlessly faces the slope portion 133a of the image pickup unit 130 as shown in FIG. 22.

Note that the fixing pin 150 is in a state that the head portion 152 projects from the stepped portion 124 as shown in FIG. 23. That is, a predetermined length is set for the fixing pin 150 relative to a length of the unit fixing hole portion 123 so that the head portion 152 projects at the stepped portion 124 of the distal end constituting portion 121 and is accommodated inside the concave portion 124a without projecting from the outer circumferential part of the distal end constituting portion 121.

In this state, the head portion 152 is fitted into the recess portion 163 of the jig 160 so that the head portion 152 of the fixing pin 150 is sandwiched between the two arm portions 162 provided on the distal end portion 161 of the jig 160 as shown in FIG. 24. Note that a longitudinal axial position of the jig 160 is adjusted so that the distal end portion 161 is fitted into the concave portion 124a formed on the stepped portion 124 of the distal end constituting portion 121, and the facing flat faces of the two arm portions 162 come into surface-contact with the respective flat portions 152a of the head portion 152 of the fixing pin 150.

That is, similar radiuses of curvature are set which cause an outer circumferential shape of the distal end portion 161 of the jig 160 and a shape of the concave portion 124a having a semi-circular cross section formed on the stepped portion 124 of the distal end constituting portion 121 to be substantially similar. At this time, the jig 160 is in a state that one side wall face of the projecting portion 165 projecting toward the distal end portion 161 side from the cylindrical body 164 is in contact with a wall face portion 124b of the stepped portion 124 of the distal end constituting portion 121.

Note that the jig 160 is set so that, in a state that the fixing pin 150 is inserted in the unit fixing hole portion 123, and the flat portion 153 of the fixing pin 150 is in contact with the slope portion 133a of the barrel portion 133 of the image pickup unit 130, one side wall face of the projecting portion 165 is in contact with the wall face portion 124b of the stepped portion 124 of the distal end constituting portion 121 in accordance with a position where the recess portion 163 of the distal end portion 161 to be fitted into the head portion 152 is formed.

That is, a position of the projecting portion 165 of the jig 160 relative to the distal end portion 161 having the two arm portions 162 and the recess portion 163 is set so that, before the fixing pin 150 is rotated, one side wall face of the projecting portion 165 comes into contact with the wall face portion 124b of the stepped portion 124 of the distal end constituting portion 121 when the head portion 152 is fitted into the recess portion 163.

Next, the jig 160 is rotated until the other side wall face of the projecting portion 165 comes into contact with a wall face portion 124c of the stepped portion 124 of the distal end constituting portion 121 from the state of FIG. 24, as shown in FIG. 25. Thereby, the fixing pin 150 is rotated by the predetermined angle θ, here, 90° to 135° around the axis.

Note that the jig 160 is such that the predetermined angle θ (90° to 135°), which is an amount of rotation of the fixing pin 150 around the axis, is specified by the other side wall face of the projecting portion 165 projecting toward the distal end portion 161 side from the cylindrical body 164 coming into contact with the wall face portion 124c of the stepped portion 124 of the distal end constituting portion 121.

That is, the jig 160 is such that a length (width) of the projecting portion 165 around the axis is set so that the predetermined angle θ (90° to 135°), which is the amount of rotation of the fixing pin 150, can be specified by, from the state that one side wall face of the projecting portion 165 is in contact with the wall face portion 124b of the stepped portion 124 of the distal end constituting portion 121, the other side wall face of the projecting portion 165 coming into contact with the wall face portion 124c of the stepped portion 124.

Then, a midway part of the rotated fixing pin 150 comes into contact with the slope portion 133a, deforms (plastically deforms) and becomes a concave deformed portion 151a as shown in FIGS. 26 and 27. That is, since the fixing pin 150 is formed with metal with a lower hardness than rigid metal forming the barrel portion 133 of the image pickup unit 130, the fixing pin 150 easily deforms without damaging the slope portion 133a of the barrel portion 133.

At this time, when the fixing pin 150 is rotated, the deformed portion 151a positively deforms toward the two circumferential grooves 155 side as shown in FIG. 28, it is possible to secure a range of contact between the fixing pin and the slope portion 133a of the barrel portion 133 and prevent variation in fixation force.

That is, by providing the circumferential grooves 155 on both side portions of contact with the slope portion 133a of the barrel portion 133 of the image pickup unit 130, the fixing pin 150 positively deforms toward the circumferential grooves 155 provided on both sides of the deformed portion 151a when rotating.

Thereby, it is possible to secure the range of contact with the slope portion 133a of the barrel portion 133 of the image pickup unit 130 by the fixing pin 150, and, therefore, it is possible to suppress variation in fixation force. Thus, the image pickup unit 130 is assembled and fixed to the distal end constituting portion 121.

At this time, the image pickup unit 130 is assembled and fixed to the distal end constituting portion 121 in a state of being given stress Fa pressing the image pickup unit 130 to the distal end side and stress Fb pressing the image pickup unit 130 to the internal diameter direction by the fixing pin 150 deformed (plastically deformed) by the slope portion 133a of the barrel portion 133.

Thus, by providing the barrel portion 133 with the slope portion 133a with which the fixing pin 150 is to come into contact, a distal-end-side end face of the barrel portion 133 is caused to come into contact with an end face around the rear end of the observation hole portion 122a forming the unit setting hole portion 122 of the distal end constituting portion 121 by receiving the thrust-direction stress Fa toward the distal end side, and an outer circumferential face of the barrel portion 133 is caused to come into contact with an internal circumferential face of the unit setting hole portion 122 toward one direction away from the fixing pin 150 by receiving the radial-direction stress Fb in the internal diameter direction when the image pickup unit 130 is fixed to the distal end constituting portion 121; and, thereby, the image pickup unit 130 is fixed at a predetermined position without backlash.

Note that the concave-shaped deformed portion 151a (see FIG. 27) formed on the fixing pin 150 is in close contact with the slope portion 133a and caught in a direction orthogonal to a longitudinal direction of the image pickup unit 130, that is, in an axial direction of the fixing pin 150, and the fixing pin 150 does not come out from the unit setting hole portion 122 unless the flat portion 153 of the pin body 151 is rotated to the original position of facing the slope portion 133a.

Further, various kinds of units are similarly fixed to the distal end constituting portion 121 though they are not shown here, and the above-described distal end cover 25 made of resin is fastened to a front face part. Furthermore, an outer cover is fastened by bobbin bonding or the like to the distal end constituting portion 121 from a proximal end of the distal end cover 25.

By the way, at time of pulling out the fixing pin 150 from the unit setting hole portion 122, it is only necessary for the flat portion 153 of the pin body 151 to be rotated to the original position of facing the slope portion 133a by the jig 160 as described above. At this time, in a state that one side wall face of the projecting portion 165 of the jig 160 is in contact with the wall face portion 124b of the stepped portion 124 of the distal end constituting portion 121, the flat portion 153 of the pin body 151 is at the position of facing the slope portion 133a. At the time of pulling out the fixing pin 150 from the unit setting hole portion 122, the fixing pin 150 can be pulled out by hooking a tool such as a hook in the hole portion 154 formed in the head portion 152.

As described above, in the part fixation structure of the endoscope 1, a center O1 of the fixing pin 150 can be arranged at a position close to an internal diameter side of the image pickup unit 130 by providing the slope portion 133a with which the fixing pin 150 is to come into contact with, on the barrel portion 133 to be a place where the image pickup unit 130 is fixed. Therefore, it is not necessary to increase an outer diameter of the barrel portion 133, and, as a result, downsizing becomes possible.

Further, by causing the center O1 of the fixing pin 150 to be positioned in the circumferential groove 133b formed on the barrel portion 133 of the lens frame 131 of the image pickup unit 130, the image pickup unit 130 can be fixed to the distal end constituting portion 121 more firmly.

Furthermore, in the part fixation structure of the endoscope 1 described above, by adopting the fixing pin 150 to be inserted and fixed in the tangential direction of the outer circumferential portion of a place where the image pickup unit 130 is to be fixed, the barrel portion 133 here, as a fixing member for fixing the image pickup unit 130 to the distal end constituting portion 121, a degree of positional freedom of the place of fixation by the fixing pin 150 increases, and thickness of the distal end constituting portion 121 can be suppressed. Therefore, a diameter of the distal end constituting portion 121 can be reduced. As a result, downsizing becomes possible, and the distal end portion 11 can be also downsized, which leads to reduction in a diameter of the insertion portion 2.

That is, a configuration in which fixation is performed by a set screw as done conventionally is a configuration in which a fixing member is inserted toward a center direction (an internal diameter direction) of the distal end constituting portion 121. Therefore, a position where a thickness of the distal end constituting portion 121 is secured is restricted, and a certain degree of thickness is required, so that the distal end constituting portion 121 is upsized.

In comparison, in the part fixation structure of the endoscope 1 of the present embodiment, the thickness of the distal end constituting portion 121 which is necessary for a fixing member is not required in comparison with the configuration in which fixation is performed with a set screw or the like as done conventionally. Therefore, a position of fixation by the fixing pin 150 is not restricted much, and it is also possible to downsize the distal end constituting portion 121.

As a result, the position where the image pickup unit 130 is fixed to the distal end constituting portion 121 is not restricted, and a degree of freedom of layout of the position where the image pickup unit 130 is fixed increases.

Further, in the part fixation structure of the endoscope 1, by forming the fixing pin 150 with material with lower hardness than material of the place where the image pickup unit 130 is fixed, the image pickup unit 130 is not damaged, and, therefore, a problem at time of reusing the image pickup unit 130 does not easily occur.

The invention described in the above embodiment is not limited to the embodiment and the modifications, and, at an implementation phase, various kinds of changes can be made within a range not departing from the spirit of the invention. Furthermore, the above embodiment includes inventions at various stages, and various inventions can be extracted by appropriately combining a plurality of constituent features disclosed.

For example, even if some constituent features are deleted from all constituent features shown in the embodiment, a configuration obtained after deleting the constituent features can be extracted as an invention if the stated problem can be solved, and the stated advantageous effects can be obtained.

What is claimed is:
1. An endoscope comprising:
 an insertion portion configured to be inserted into a subject;
 a distal end cover provided on a distal end of the insertion portion;
 a holding member fitted with the distal end cover;

a cylindrical member configured to be inserted into the distal end cover and the holding member, the cylindrical member having a V groove formed on an outer circumference;

an elastically deformable pin configured to be engageably inserted into the V groove of the cylindrical member and to fix the cylindrical member relative to the distal end cover and the holding member;

a first accommodating groove in which the pin is set; and a second accommodating groove in communication with a central portion of the first accommodating groove, the second accommodating groove having a longitudinal-direction length shorter than a longitudinal-direction length of the first accommodating groove, the second accommodating groove being configured to accommodate a portion of the pin other than first and second ends of the pin, wherein the pin is set in the first accommodating groove and the portion of the pin is accommodated in the second accommodating groove in a bent state when the portion of the pin comes into contact with the V groove of the cylindrical member so as to press the cylindrical member with a predetermined strength by a restoring force, to thereby fix the cylindrical member relative to the distal end cover and the holding member.

2. The endoscope according to claim 1, wherein the first accommodating groove and the second accommodating groove are formed on the surface of the holding member.

3. The endoscope according to claim 2, wherein the first accommodating groove is a concave groove.

4. The endoscope according to claim 2, wherein the first accommodating groove and the second accommodating groove are also formed on a back surface of the distal end cover facing the surface of the holding member.

5. An insertion portion for an endoscope, the insertion portion comprising:

a distal end cover;

a holding member fitted with the distal end cover;

a cylindrical member configured to be inserted into the distal end cover and the holding member, the cylindrical member having a V groove formed on an outer circumference;

an elastically deformable pin configured to be engageably inserted into the V groove of the cylindrical member and to fix the cylindrical member relative to the distal end cover and the holding member;

a first accommodating groove formed in which the pin is set; and a second accommodating groove in communication with a central portion of the first accommodating groove, the second accommodating groove having a longitudinal-direction length shorter than a longitudinal-direction length of the first accommodating groove, the second accommodating groove being configured to accommodate a portion of the pin other than first and second ends of the pin, wherein the pin is set in the first accommodating groove and the portion of the pin is accommodated in the second accommodating groove in a bent state when the portion of the pin comes into contact with the V groove of the cylindrical member so as to press the cylindrical member with a predetermined strength by a restoring force, to thereby fix the cylindrical member relative to the distal end cover and the holding member.

* * * * *